(12) United States Patent
Armstrong

(10) Patent No.: US 11,964,039 B2
(45) Date of Patent: *Apr. 23, 2024

(54) COMPOSITIONS THAT BRIGHTEN SKIN, PROVIDE SUN PROTECTION, AND PERMIT VITAMIN D PRODUCTION

(71) Applicant: Ernest T. Armstrong, El Paso, TX (US)

(72) Inventor: Ernest T. Armstrong, El Paso, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/391,738

(22) Filed: Aug. 2, 2021

(65) Prior Publication Data
US 2022/0016010 A1    Jan. 20, 2022

Related U.S. Application Data

(63) Continuation of application No. 16/071,658, filed as application No. PCT/AU2017/050051 on Jan. 23, 2017, now Pat. No. 11,077,044.

(30) Foreign Application Priority Data

Jan. 22, 2016    (AU) ................................ 2016900200

(51) Int. Cl.
| | | |
|---|---|---|
| *A61K 8/49* | (2006.01) | |
| *A61K 8/34* | (2006.01) | |
| *A61K 8/35* | (2006.01) | |
| *A61K 8/37* | (2006.01) | |
| *A61K 8/42* | (2006.01) | |
| *A61K 8/44* | (2006.01) | |
| *A61K 8/46* | (2006.01) | |
| *A61K 8/60* | (2006.01) | |
| *A61K 8/67* | (2006.01) | |
| *A61Q 17/04* | (2006.01) | |
| *A61Q 19/02* | (2006.01) | |

(52) U.S. Cl.
CPC ............ *A61K 8/4946* (2013.01); *A61K 8/345* (2013.01); *A61K 8/347* (2013.01); *A61K 8/35* (2013.01); *A61K 8/37* (2013.01); *A61K 8/42* (2013.01); *A61K 8/44* (2013.01); *A61K 8/466* (2013.01); *A61K 8/4926* (2013.01); *A61K 8/60* (2013.01); *A61K 8/675* (2013.01); *A61K 8/676* (2013.01); *A61Q 17/04* (2013.01); *A61Q 19/02* (2013.01)

(58) Field of Classification Search
CPC ...... A61K 8/4946; A61K 8/347; A61K 8/675; A61K 8/4926; A61K 8/44; A61K 8/345; A61K 8/35; A61K 8/37; A61K 8/42; A61K 8/466; A61K 8/60; A61Q 17/04; A61Q 19/02
See application file for complete search history.

(56) References Cited

U.S. PATENT DOCUMENTS

| | | |
|---|---|---|
| 6,015,548 A | 1/2000 | Siddiqui et al. |
| 2003/0180237 A1* | 9/2003 | Lersch ................. A61K 8/494 424/62 |
| 2007/0274932 A1 | 11/2007 | Suginaka et al. |
| 2010/0305168 A1 | 12/2010 | Robinson et al. |
| 2013/0156711 A1 | 6/2013 | Castro |
| 2013/0243836 A1 | 9/2013 | Tanner et al. |
| 2014/0178314 A1 | 6/2014 | Tanner et al. |
| 2015/0023895 A1 | 1/2015 | Finley et al. |
| 2015/0064122 A1 | 3/2015 | Meyer et al. |

FOREIGN PATENT DOCUMENTS

| | | | | |
|---|---|---|---|---|
| EP | 1764083 | | 3/2007 | |
| EP | 2789369 | | 10/2014 | |
| EP | 2789369 A1 | * | 10/2014 | ........... A61K 31/365 |
| WO | 2011109505 | | 9/2011 | |

OTHER PUBLICATIONS

International Search Report and Written Opinion for Int'l Patent Appln No. PCT/AU2017/050051, dated Apr. 12, 2017, 10 pages, Australian Patent Office, International Bureau.
Extended European Search Report for PCT/AU2017/050051, dated May 27, 2019, 8 pages, European Patent Office.
Mintel Group Ltd., Day Cream SPF, Product Description , Dec. 2013.

* cited by examiner

*Primary Examiner* — Jianfeng Song
(74) *Attorney, Agent, or Firm* — Ryder, Mazzeo & Konieczny LLC; Douglas J. Ryder

(57) ABSTRACT

The present invention relates to sunscreen compositions. More specifically, the present invention relates to sunscreen compositions that, when applied to the skin, prevent sun damage while allowing the passage of sufficient UVB in the range of 290 nm-298 nm to produce vitamin D, while also inhibiting melanogenesis.

15 Claims, No Drawings

COMPOSITIONS THAT BRIGHTEN SKIN, PROVIDE SUN PROTECTION, AND PERMIT VITAMIN D PRODUCTION

BACKGROUND

Excessive skin exposure to ultraviolet radiation (UVR) is associated with basal cell and squamous-cell cancers. Skin may become damaged and wrinkled when excessive numbers of photons in the UVB (290-320 nm) and UVA (320-400 nm) ranges damage DNA via photochemical pyrimidine dimer disruption and diminish the elastic properties of collagen.

Human skin reacts differently to ultraviolet A radiation (400 nm to 320 nm; UVA) than it does to ultraviolet B radiation (320 nm to 290 nm UVB). Rays of light in the UVA wavelength range penetrate deep into the dermis of the skin where they damage collagen fibers, reduce elasticity, cause wrinkles, and generally advance photo ageing. UVA with a wavelength of about 350 nm causes the oxidation of the melanin that already exists in the skin, resulting in darker skin. This UVA-induced skin darkening becomes noticeable within 2 to 5 hours, and subsides within several days. UVA exposure, however, does not increase the quantity of melanin, the skin's pigment responsible for dark spots and a tan (facultative pigmentation).

In contrast to UVA, UVB penetrates only as far down into the skin as the basal layer of the epidermis, leaving the collagen unaffected. Exposure to UVB precipitates melanogenesis, the process that causes specialized skin cells called melanocytes to increase the quantity of melanin in the skin, thereby resulting in facultative pigmentation. This UVB-induced skin darkening becomes noticeable within 48 to 72 hours after exposure, and subsides within several weeks to several months. UVB, through melanogenesis, is responsible for tanning, as well as dark hyperpigmentation patches on human skin that include liver spots, sunspots, age spots, red spots, brown spots, dark spots, senile freckles, lentigos, solar lentigines, and blemishes. Interestingly, the melanin also behaves as a UVR filtering agent by absorbing UVB.

There is also a relationship between UVB exposure and vitamin D levels in humans. Synthesis of a precursor of vitamin D occurs in the skin when UVB, and in particular, UVB with a wavelength in the range of 290 nm-298 nm, is used to break a strong chemical bond in a cholesterol-like molecule. Higher levels of vitamin D in the body correlate to lower rates of various diseases, including multiple sclerosis, diabetes, rheumatoid arthritis, bone disease, cardiovascular problems and cancer.

Vitamin D is synthesized mostly in the stratum spinosum and stratum basale of the skin, whilst melanogenesis is initiated farther down in the basale layer. UVB in the 290 nm to 315 nm range penetrates the epidermis only to a limited depth before being absorbed. This range can be divided in two, with the shorter wavelengths (290 nm to 298 nm) favoring vitamin D production and with the longer wavelengths (299 nm to 315 nm) favoring melanogenesis. The longer the wavelength the deeper the penetration.

Humans obtain most of their vitamin D requirement from casual exposure to sunlight. However, modern living has impacted upon the exposure humans are having to beneficial UVB responsible for vitamin D production. As UVB comes from the sun 90% to 95% of it is absorbed by atmospheric ozone. Of the 10% to 5% of UVB that reaches the earth's surface; haze attenuates another 5% to 23%, overcast conditions attenuate another 50% to 70%, and cumulus clouds attenuate as much as 99%. UVB in amounts that can produce biologically significant quantities of vitamin D arrive at the surface of the Earth only when the sun is high in the sky, usually between about 11 a.m. and about 1 p.m. Glass in buildings and vehicles filters close to 100% of the UVB radiation. Further to this, typically when humans are exposed to an appreciable amount of UVB during outdoor activities, it is likely this beneficial vitamin D production is being prevented by the application of sunscreens.

Sunscreens are made up of combinations of UVR filtering agents, wherein each UVR filtering agent absorbs, blocks or reflects a unique spectrum of light and combining various UVR filtering agents in different percentages results in different types of sunscreens. Conventional sunscreens are designed to filter the broadest spectrum of UVR across the UVB and UVA wavelengths possible. However, in doing this, sunscreens screen a high percentage of the UVB human skin uses for vitamin D synthesis.

Modern, indoor lifestyles combined with excessive use of sunscreens have contributed to increasing reported rates of vitamin D deficiency in many countries. Vitamin D deficiency is defined as having a 25-hydroxyvitamin D blood level below 20 ng/ml and vitamin D insufficiency is between 21 and 29 ng/mL (Holick, M F, The vitamin D solution Hudson Street Press, 2010, p. 46).

Despite the advantages of sensible sun exposure, many cultures associate lighter skin with a higher socio-economic status while many individuals find skin which is free of dark spots to be more beautiful than sun-blemished skin. Views about skin lightness are quite different between Eastern and Western cultures. In many parts of Asia and the Indian sub-continent both men and women wish to increase their social status by recoloring their skin. In 2004 a marketing study by Synovate estimated that some 40 percent of women in Taiwan, Hong Kong, South Korea, Malaysia and the Philippines used skin lightening products. Accordingly, these populations actively avoid any sun exposure and are more susceptible to vitamin D deficiencies.

While recent advances in sunscreen technology have allowed for the user to be protected against the majority of damaging UVR whilst still producing a therapeutic dose of Vitamin D (see PCT/IB2009/055881), this invention inevitably leads to the development of facultative pigmentation (a tan), which is not desirable in many cultures that perceive whiter or brighter skin to be more beautiful.

The present invention is surprising in view of PCT/IB2009/055881, because rather than encourage facultative pigmentation, which inevitably reduces the skin's capacity to produce of vitamin D by virtue of the melanin essentially behaving as a UVR filtering agent and. preventing UVB wavelengths from penetrating the skin, the present compositions impair melanogenesis.

SUMMARY

The current invention relates to sunscreen compositions that prevent facultative pigmentation (i.e., tanning) and protect the skin from sun damage, whilst also permitting the skin to produce vitamin D. The development of any such composition is innately problematic and counter-intuitive because tanning and vitamin D production are effectuated by essentially the same spectrum of UVB light.

Accordingly, in a first aspect of the present invention, there is provided a topical sunscreen composition that prevents UVR-induced skin damage and is adapted to allow passage of sufficient UVB in the range of 290 nm-298 nm to produce vitamin D, while also inhibiting melanogenesis.

The sunscreen compositions comprise UVR filtering agents, the combinations and concentrations of which are adapted, based on the absorbance spectra of each agent, to selectively filter enough light in the UVB and UVA ranges to prevent skin damage whilst permitting passage of enough UVB in the range of 290 nm-298 nm to permit vitamin D production.

It would be understood that the wavelength range of 290 nm-298 nm is significant because this is the UVR wavelength that, upon absorption by the skin of a human subject, results in the highest production of vitamin D by said human.

The sunscreen compositions of the invention are suitable for topical administration and may be in the form of a liquid, lotion, emulsion, mousse, paste, cream, serum, spray, ointment, gel, foam, or balm.

In order for a sunscreen to be effective, it needs to adequately cover the skin. Accordingly, in preferred embodiments of the present invention, the composition is to be applied the skin at a rate of about 0.01 mg/cm$^2$-50 mg/cm$^2$, or about 0.05 mg/cm$^2$-20 mg/cm$^2$ or about 0.05 mg/cm$^2$-10 mg/cm$^2$ or about 0.05 mg/cm$^2$-5 mg/cm$^2$. Preferably, the composition is to be applied to the skin at a rate of at least about 0.5 mg/cm$^2$-2 mg/cm$^2$. Preferably, the composition is to be applied to the skin at a rate of at least about 0.5 mg/cm$^2$. More preferably, the composition is to be applied to the skin at a rate of at least about 1 mg/cm$^2$. Preferably, the composition is to be applied to the skin at a rate of at least about 1.3 mg/cm$^2$ to about 2 mg/cm$^2$. Even more preferably, the composition is to be applied to the skin at a rate of at least about 2 mg/cm$^2$. The person of skill in the art would understand that the application rate of at least about 2 mg/cm$^2$ may be significant because this is the hypothetical amount of a sunscreen composition that preferably needs to be applied to the skin of a test subject in order to achieve an SPF rating in accordance with at least ISO 24444, E.U. and Australian in vivo testing methods.

The efficacy of a particular sunscreen composition may be expressed by the SPF, which is defined as the UVR energy required to produce a minimal erythemal dose (MED; i.e., sunburn) in skin with the sunscreen applied to it, divided by the UVR energy required to produce an MED in skin without the sunscreen. The MED is defined as the lowest time interval or dosage of UVR sufficient to produce a minimal, perceptible sunburn on skin with no sunscreen. As such, SPF is a relative value based on how long it would take for the user to sustain sunburn when wearing the sunscreen, versus how long it would take without the sunscreen. For instance, someone using a sunscreen with an SPF of 15 will take 15 times longer to sustain sunburn than without the sunscreen. The higher the SPF, the higher the protection from UVR afforded by the sunscreen composition.

In one or more embodiments of the present invention, the sunscreen composition has an SPF of at least 4, at least 6, at least 8, at least 10, at least 15, at least 20, at least 25, at least 30, at least 40 or at least 50. Preferably, the composition has an SPF of at least 10, and more preferably, at least 15. In other preferred embodiments, the sunscreen composition has an SPF of at least 20, at least 25 or at least 30. The SPF may be determined in accordance with the standards defined in AS/NZS 2604:2012, which correlates to the true SPF of the product when applied to the skin at a rate of 2 mg/cm$^2$.

The skilled addressee would appreciate that the skin is made up of layers, including the epidermis, dermis and hypodermis (subcutaneous layer), as well as other cell types and components such as adipose tissue, hair follicles, veins, arteries, sweat glands and nerve fibers.

By UVR-induced skin damage is meant any temporary or permanent damage to the skin or cells in the skin or to the appearance of the skin or the cells in the skin layers, such as, for example, dry skin, erythema (sunburn), keratosis, wrinkles, hyperpigmentation, premature aging, and DNA damage to cells in the skin. The hyperpigmentation of the skin can manifest in what are commonly known as sunspots, age spots, liver spots, senile freckles, lentigos, solar lentigines and blemishes.

In embodiments of the invention, the compositions comprise two or more UVR filtering agents. The UVR filtering agents, and the concentrations of the UVR filtering agents in the compositions, are selected and adapted based on the desired properties of the compositions of the invention. That is, the UVR, filtering agents are selected, and their concentrations adapted such that the compositions of the invention are effective at preventing UVR-induced skin damage, whilst also allowing the passage of sufficient UVB in the range of 290 nm-298 nm to permit the production of vitamin D in the skin of a human exposed to UVR.

In embodiments of the invention, the sunscreen compositions permit the passage of at least 5%, at least 10%, at least 15% or at least 20% of the UVB light at approximately 290 nm-298 nm (the wavelength range for maximum vitamin D production).

In preferred embodiments of the invention, the sunscreen compositions permit the passage of about 5% to about 25% of the UVB light at approximately 290 nm-298 nm (the wavelength range for maximum vitamin D production).

The UVR filtering agents used in the compositions of the present invention may be any compound that has the capacity to absorb, block or reflect UVR, wherein the UVR occurs at a wavelength within the range of about 280 nm to about 400 nm. It would be understood by the person skilled in the art that this wavelength range encompasses both the UVA and UVB wavelength range, and therefore encompasses the range of UVR that induces sun-damage to the skin of humans.

The UVR filtering agent may be a chemical sun screening agent or a physical sun screening agent. In addition to those discussed above, the choice of UVR filtering agent or agents used in the composition would be influenced by factors such as desired SPF rating, desired absorption in the wavelength range of 290 nm-298 nm, safety and regulatory considerations, whether the agents were liquid or solid, and the capability of the UVR filtering agent(s) to be combined with the other components to form a stable composition.

In embodiments of the invention, the compositions comprise one or more UVR filtering agents that are chemical sun screening agents that absorb UVR selected from the group consisting of menthyl anthranilate, sulisobenzone (benzophenone-4), sulisobenzone sodium (benzophenone-5), diethylamino hydroxybenzoyl hexyl benzoate, oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), Polysilicone-15 (dimethico-diethylbenzal malonate), disodium phenyl dibenzimidazole tetrasulfonate, PEG-25 PABA (Ethoxylated ethyl 4-aminobenzoate), homosalate (homomenthyl salicylate) and octyl salicylate salicylate).

The preceding list is a compilation of selected UVR filtering agents approved for use in, for example, Australia, the U.S., Europe and Japan, and this list may change over time to exclude some compounds, while new compounds may be included. It would be understood that any compounds added to the list would also he suitable UVR filtering agents for use in the present invention.

In embodiments of the present invention, the composition comprises at least two UVR filtering agents selected from the group consisting of menthyl anthranilate, sulisobenzone (benzophenone-4), sulisobenzone sodium (benzophenone-5), diethylamino hydroxybenzoyl hexyl benzoate, oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), Polysilicone-15 (dimethico-diethylbenzal malonate), disodium phenyl dibenzimidazole tetrasulfonate, PEG-25 PABA (Ethoxylated ethyl 4-aminobenzoate), homosalate (homomenthyl salicylate) and octyl salicylate (ethyl hexyl salicylate).

In embodiments of the present invention, the composition comprises at least two UVR filtering agents selected from the group consisting of oxybenzone (benzophenone-3), ecamsule (terephthalylidene dicamphor sulfonic acid), octocrylene (2-ethyl hexyl alpha-cyano-beta-phenylcinnamate), butyl methoxy dibenzoylmethane (avobenzone), homosalate (homomenthyl salicylate;) and octyl salicylate (ethylhexyl salicylate).

In embodiments of the present invention, the composition comprises at least three UVR filtering agents selected from the group consisting of oxybenzone (benzophenone-3), ecamsule (terephthalylidene dicamphor sulfonic acid), octocrylene (2-ethyl hexyl alpha-cyano beta-phenylcinnamate), butyl methoxy dibenzoylmethane (avobenzone), homosalate (homomenthyl salicylate) and octyl salicylate (ethylhexyl salicylate).

In embodiments of the present invention, the composition comprises at least three UVR filtering agents selected from the group consisting of menthyl anthranilate, sulisobenzone (benzophenone-4), sulisobenzone sodium (benzophenone-5), diethyamino hydroxybenzoyl hexyl benzoate, oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), Polysilicone-15 (dimethico-diethylbenzal malonate), disodium phenyl dibenzimidazole tetrasulfonate, PEG-25 PABA (Ethoxylated ethyl 4-aminobenzoate), homosalate (homomenthyl salicylate) and octyl salicylate (ethylhexyl salicylate).

In embodiments of the present invention, the composition comprises menthyl anthranilate at a concentration of about 0.5% to about 7% (w/w). In preferred embodiments of the invention, the composition comprises menthyl anthranilate at a concentration of about 1% to about 4% (w/w).

In embodiments of the present invention, the composition comprises sulisobenzone (benzophenone-4) at a concentration of about 0.5% to about 10% (w/w). In preferred embodiments of the invention, the composition comprises sulisobenzone (benzophenone-4) at a concentration of about 1% to about 4% (w/w).

In embodiments of the present invention, the composition comprises sulisobenzone sodium (benzophenone-5) at a concentration of about 0.5% to about 10% (w/w). In preferred embodiments of the invention, the composition comprises sulisobenzone sodium (benzophenone-5) at a concentration of about 1% to about 4% (w/w).

In embodiments of the present invention, the composition comprises diethylamino hydroxybenzoyl hexyl benzoate at a concentration of about 0.5% to about 10% (w/w). In preferred embodiments of the invention, the composition comprises diethylamino hydroxybenzoyl hexyl benzoate at a concentration of about 1% to about 5% (w/w).

In embodiments of the present invention, the composition comprises oxybenzone (benzophenone-3) at a concentration of about 0.5% to about 8% (w/w). In preferred embodiments of the invention, the composition comprises oxybenzone (benzophenone-3) at a concentration of about 1% to about 4% (w/w).

In embodiments of the present invention, the composition comprises ecamsule (terephthalylidene dicamphor sulfonic acid) at a concentration of about 0.5% to about 10% (w/w). In preferred embodiments of the invention, the composition comprises ecamsule (terephthalylidene dicamphor sulfonic acid) at a concentration of about 1% to about 9% (w/w).

In embodiments of the present invention, the composition comprises octocrylene (2-ethylhexyl alpha-cyano-beta-phenylcinnamate) at a concentration of about 0.5% to about 10% (w/w). In preferred embodiments of the invention, the composition comprises octocrylene (2-ethylhexyl alpha-cyano-beta-phenylcinnamate) at a concentration of about 1% to about 7% (w/w).

In embodiments of the present invention, the composition comprises butyl methoxy dibenzonethane (avobenzone) at a concentration of about 0.5% to about 7% (w/w). In preferred embodiments of the invention, the composition comprises butyl methoxy dibenzoylmethane (avobenzone) at a concentration of about 1% to about 5% (w/w).

In embodiments of the present invention, the composition comprises polysilicone-15 (dimethico-diethylbenzal malonate) at a concentration of about 0.5% to about 5% (w/w). In preferred embodiments of the invention, the composition comprises polysilicone-15 (dimethico-diethylbenzal malonate) at a concentration of about 1% to about 3% (w/w).

In embodiments of the present invention, the composition comprises disodium phenyl dibenzimidazole tetrasulfonate at a concentration of about 0.5% to about 5% (w/w). In preferred embodiments of the invention, the composition comprises disodium phenyl dibenzimidazole tetrasulfonate at a concentration of about 1% to about 3% (w/w).

In embodiments of the present invention, the composition comprises PEG-25 PABA (Ethoxylated ethyl 4-aminobenzoate) at a concentration of about 0.5% to about 5% (w/w). In preferred embodiments of the invention, the composition comprises PEG-25 PABA (Ethoxylated ethyl 4-aminobenzoate) at a concentration of about 2% to about 3% (w/w).

In embodiments of the present invention, the composition comprises homosalate (homomenthyl salicylate) at a concentration of about 0.5% to about 15% (w/w). In preferred embodiments of the invention, the composition comprises homosalate (homomenthyl salicylate) at a concentration of about 1% to about 13% (w/w). In other preferred embodiments of the invention, the composition comprises homosalate (homomenthyl salicylate) at a concentration of about 0.5% to about 6% (w/w).

In embodiments of the present invention, the composition comprises octyl salicylate (ethylhexyl salicylate) at a concentration of about 0.5% to about 10% (w/w). In preferred embodiments of the invention, the composition comprises octyl salicylate (ethylhexyl salicylate) at a concentration of about 0.5% to about 8% (w/w). In other preferred embodiments of the invention, the composition comprises octyl salicylate (ethyl hexyl salicylate) at a concentration of about 0.5% to about 6% (w/w).

In embodiments of the present invention, the composition comprises at least two UVR filtering agents selected from the group consisting of oxybenzone (benzophenone-3), ecamsule (terephthalylidene dicamphor sulfonic acid), octocrylene (2-ethyl hexyl alpha-cyano-beta-phenylcinnamate), butyl methoxy dibenzoylmethane (avobenzone), homosalate (homomenthyl salicylate) and octyl salicylate (ethylhexyl salicylate), wherein, when present, the composition comprises oxybenzone (benzophenone-3) at a concentration of about 0.5% to about 8% (w/w), the composition comprises ecamsule (terepththalylidene dicamphor sulfonic acid) at a concentration of about 0.5% to about 10% (w/w), the composition comprises octocrylene (2-ethylhexyl alpha-cyano-beta-phenylcinnamate) at a concentration of about 0.5% to about 10% (w/w), the composition comprises butyl methoxy dibenzoylmethane (avobenzone) at a concentration of about 0.5% to about 7% (w/w), the composition comprises homosalate (homomenthyl salicylate) at a concentration of about 0.5% to about 15% (w/w), the composition comprises octyl salicylate (ethylhexyl salicylate) at a concentration of about 0.5% to about 10% (w/w).

In embodiments of the present invention, the composition comprises at least three UVR filtering agents selected from the group consisting of oxybenzone (benzophenone-3), ecamsule (terephthalylidene dicamphor sulfonic acid), octocrylene (2-ethylhexyl alpha-cyano-beta-phenyl cinnamate), butyl methoxy dibenzoylmethane (avobenzone), homosalate (homomenthyl salicylate) and octyl salicylate (ethylhexyl salicylate), wherein, when present, the composition comprises oxybenzone (benzophenone-3) at a concentration of about 0.5% to about 8% (w/w), the composition comprises ecamsule (terephthalylidene dicamphor sulfonic acid) at a concentration of about 0.5% to about 10% (w/w), the composition comprises octocrylene (2-ethylhexyl alpha-cyano-beta-phenylcinnamate) at a concentration of about 0.5% to about 10% (w/w), the composition comprises butyl methoxy dibenzoylmethane (avobenzone) at a concentration of about 0.5% to about 7% (w/w), the composition comprises homosalate (homomenthyl salicylate) at a concentration of about 0.5% to about 15% (w/w), the composition comprises octyl salicylate (ethylhexyl salicylate) at a concentration of about 0.5% to about 10% (w/w).

In preferred embodiments of the present invention, the composition comprises at least two UVR filtering agents selected from the group consisting of oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), homosalate (homomenthyl salicylate) and octyl salicylate (ethylhexyl salicylate), wherein, when present, the composition comprises oxybenzone (benzophenone-3) at a concentration of about 1% to about 4% (w/w), the composition comprises ecamsule (terephthalylidene dicamphor sulfonic acid) at a concentration of about 1% to about 9% (w/w), the composition comprises octocrylene (2-ethylhexyl alpha-cyano-beta-phenylcinnamate) at a concentration of about 1% to about 7% (w/w), the composition comprises butyl methoxy dibenzoylmethane (avobenzone) at a concentration of about 1% to about 5% (w/w), the composition comprises homosalate (homomenthyl salicylate) at a concentration of about 0.5% to about 6% (w/w), the composition comprises octyl salicylate (ethylhexyl salicylate) at a concentration of about 0.5% to about 6% (w/w).

In preferred embodiments of the present invention, the composition comprises at least three UVR filtering agents selected from the group consisting of oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), homosalate (homomenthyl salicylate) and octyl salicylate (ethylhexyl salicylate), wherein, when present, the composition comprises oxybenzone (benzophenone-3) at a concentration of about 1% to about 4% (w/w), the composition comprises ecamsule (terephthalylidene dicamphor sulfonic acid) at a concentration of about 1% to about 9% (w/w), the composition comprises octocrylene (2-ethylhexyl alpha-cyano-beta-phenylcinnamate) at a concentration of about 1% to about 7% (w/w), the composition comprises butyl methoxy dibenzoylmethane (avobenzone) at a concentration of about 1% to about 5% (w/w), the composition comprises homosalate (homomenthyl salicylate) at a concentration of about 0.5% to about 6% (w/w), the composition comprises octyl salicylate (ethylhexyl salicylate) at a concentration of about 0.5% to about 6% (w/w).

In general, the UVR filtering agents used in the compositions of the present invention can be classified as those that primarily absorb UVA, such as menthyl anthranilate, diethylamino hydroxybenzoyl hexyl benzoate, ecamsule (terephthalylidene dicamphor sulfonic acid), butyl methoxy dibenzoymethane (avobenzone), and disodium phenyl dibenzimidazole tetrasulfonate, and those that primarily absorb UVB, sulisobenzone (benzophenone-4), sulisobenzone sodium (benzophenone-5), oxybenzone (benzophenone-3), octocrylene (2-ethyl hexyl alpha-cyano-beta-phenylcinnamate), Polysilicone-15 (dimethico-diethylbenzal malonate), PEG-25 PABA (Ethoxylated ethyl 4-aminobenzoate), homosalate (homomenthyl salicylate) and octyl salicylate (ethylhexyl salicylate).

In embodiments of the present invention, the composition comprises at least one UVA filtering agent selected from the group consisting of menthyl anthranilate, diethyl amino hydroxybenzoyl hexyl benzoate, ecamsule (terephthalylidene dicamphor sulfonic acid), butyl methoxy dibenzoylmethane (avobenzone), and disodium phenyl dibenzimidazole tetrasulfonate.

In embodiments of the present invention, the composition comprises at least one UVB filtering agent selected from the group consisting of sulisobenzone (benzophenone-4), sulisobenzone sodium (benzophenone-5), oxybenzone (benzophenone-3), octocrylene (2-ethylhexyl alpha-cyano-beta-phenylcinnamate), Polysilicone-15 (dimethico-diethylbenzal malonate), PEG-25 PABA (Ethoxylated ethyl 4-aminobenzoate), homosalate (homomenthyl salicylate) and octyl salicylate (ethylhexyl salicylate).

In embodiments of the present invention, the composition comprises at least two UVB filtering agents selected from the group consisting of sulisobenzone (benzophenone-4), sulisobenzone sodium (benzophenone-5), oxybenzone (benzophenone-3), octocrylene (2-ethylhexyl alpha-cyano-beta-phenylcinnamate), Polysilicone-15 (dimethico-diethylbenzal malonate), PEG-25 PABA (Ethoxylated ethyl 4-aminobenzoate), homosalate (homomenthyl salicylate) and octyl salicylate (ethylhexyl salicylate).

In embodiments of the present invention, the composition comprises at least three UVB filtering agents selected from the group consisting of sulisobenzone (benzophenone-4), sulisobenzone sodium (benzophenone-5), oxybenzone (benzophenone-3), octocrylene (2-ethylhexyl alpha-cyano-beta-phenylcinnamate), Polysilicone-15 (dimethico-diethylbenzal malonate), PEG-25 PABA (Ethoxylated ethyl 4-aminobenzoate), homosalate (homomenthyl salicylate) and octyl salicylate (ethylhexyl salicylate).

In embodiments of the present invention, the compositions comprise at least one UVA filtering agent and at least one UVB filtering agent. For example, the composition may comprise avobenzone and homosalate, or avobenzone and octocrylene, or avobenzone and octyl salicylate, or menthyl anthranilate and homosalate, or diethylamino hydroxybenzoyl hexyl benzoate and homosalate, or ecamsule and octyl salicate, or disodium phenyl dibenzimidazole tetrasulfonate and sulisobenzone, or menthyl anthranilate and octocrylene, or ecamsule and homosalate.

In embodiments of the present invention, the compositions comprise at least one UVA filtering agent and at least two UVB filtering agents. For example, the composition may comprise avobenzone, homosalate and octocrylene, or avobenzone, octocrylene and octyl salicylate, or avobenzone, octyl salicylate and homosalate, or menthyl anthranilate, homosalate and octocrylene, or diethylamine hydroxybenzoyl hexyl benzoate, homosalate and oxybenzone, or ecamsule, octyl salicylate and homosalate, or disodium phenyl dibenzimidazole tetrasulfonate, sulisobenzone and polysilicone-15, or menthyl anthranilate, octocrylene and PEG-25 PABA, or ecamsule, homosalate and octyl salicylate.

In embodiments of the present invention, the compositions comprise at least one UVA filtering agent and at least three UVB filtering agents. For example, the composition may comprise avobenzone, homosalate, salicylate and octocrylene, or avobenzone, octocrylene, oxybenzone and octyl salicylate, or avobenzone, sulisobenzone, octyl salicylate and homosalate, or menthyl anthranilate, oxybenzone, homosalate and octocrylene, or diethylamino hydroxybenzoyl hexyl benzoate, homosalate, PEG-25 PABA and oxybenzone, or ecamsule, octyl salicylate, Polysilicone-15 and homosalate, or disodium phenyl dibenzimidazole tetrasulfonate, sulisobenzone, octocrylene and polysilicone-15, or menthyl anthranilate, oxybenzone, octocrylene and PEG-25 PABA, or ecamsule, homosalate, octocrylene and octyl salicylate.

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w) and octocrylene at a concentration of about 0.5% to about 10% (w/w).

In preferred embodiments of the invention, the composition comprises avobenzone at a concentration of about 0.5% to about 5% (w/w), homosalate at a concentration of about 0.5% to about 8% (w/w), octyl salicylate at a concentration of about 0.5% to about 6% (w/w) and octocrylene at a concentration of about 0.5% to about 7% (w/w).

In preferred embodiments of the invention, the composition comprises avobenzone at a concentration of about 1% to about 5% (w/w), homosalate at a concentration of about 1% to about 8% (w/w), octyl salicylate at a concentration of about 1% to about 8% (w/w), octocrylene at a concentration of about 1% to about 9% (w/w), and oxybenzone 1% to about 10% (w/w).

In preferred embodiments of the invention, the composition comprises avobenzone at a concentration of about 1% to about 5% (w/w), homosalate at a concentration of about 1% to about 8% (w/w), octyl salicylate at a concentration of about 1% to about 8% (w/w), octocrylene at a concentration of about 1% to about 9% (w/w), and ecamsule 1% to about 7% (w/w).

In more preferred embodiments of the invention, the composition comprises avobenzone at a concentration of about 0.5% to about 4% (w/w), homosalate at a concentration of about 0.5% to about 6% (w/w), octyl salicylate at a concentration of about 0.5% to about 3% (w/w) and octocrylene at a concentration of about 0.5% to about 4% (w/w).

In preferred embodiments of the invention, the composition comprises avobenzone at a concentration of about 1% to about 5% (w/w), homosalate at a concentration of about 1% to about 8% (w/w), octyl salicylate at a concentration of about 1% to about 8% (w/w), and octocrylene at a concentration of about 1% to about 9% (w/w).

In preferred embodiments of the invention, the composition comprises avobenzone at a concentration of about 3% to about 5% (w/w), homosalate at a concentration of about 4.9% to about 7% (w/w), octyl salicylate at a concentration of about 2.3% to about 5% (w/w), and octocrylene at a concentration of about 2.7% to about 7% (w/w).

In preferred embodiments of the invention, the composition comprises avobenzone at a concentration of about 3% (w/w), homosalate at a concentration of about 4.9% (w/w), octyl salicylate at a concentrations of about 2.3% (w/w), and octocrylene at a concentration of about 2.7% (w/w).

In preferred embodiments of the invention, the composition comprises avobenzone at a concentration of about 3% (w/w), homosalate at a concentration of about 4.9% (w/w), octyl salicylate at a concentration of about 3.7% (w/w), and octocrylene at a concentration of about 5% (w/w).

In preferred embodiments of the invention, the composition comprises avobenzone at a concentration of about 3% (w/w), homosalate at a concentration of about 6% octyl salicylate at a concentration of about 4% (w/w), and octocrylene at a concentration of about 7% (w/w).

In embodiments of the invention, the composition comprises avobenzone at a concentration of about 0.5% to about 7% (w/w), oxybenzone at a concentration of about 0.5% to about 8% (w/w), octyl salicylate at a concentration of about 0.5% to about 10% (w/w) and octocrylene at a concentration of about 0.5% to about 10% (w/w).

In preferred embodiments of the invention, the composition comprises avobenzone at a concentration of about 3% to about 5% (w/w), oxybenzone at a concentration of about 2% to about 4% (w/w), octyl salicylate at a concentration of about 2% to about 6% (w/w) and octocrylene at a concentration of about 2% to about 7%.

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w) and sulisobenzone at a concentration of about 0.5% to about 10% (w/w).

In preferred embodiments of the invention, the composition comprises avobenzone at a concentration of about 3% to about 5% (w/w), homosalate at a concentration of about 2% to about 6% (w/w), octyl salicylate at a concentration of about 2% to about 6% (w/w) and sulisobenzone at a concentration of about 2% to about 5%.

In embodiments of the invention, the composition comprises menthyl anthranilate at a concentration of about 0.5% to about 7% (w/w), homosalate at a concentration of about 0.5% to about 15% (w/w), oxybenzone at a concentration of about 0.5% to about 8% (w/w) and octocrylene at a concentration of about 0.5% to about 10% (w/w).

In preferred embodiments of the invention, the composition comprises menthyl anthranilate at a concentration of about 2% to about 4% (w/w), homosalate at a concentration of about 2% to about 6% (w/w), oxybenzone at a concentration of about 2% to about 4% (w/w) and octocrylene at a concentration of about 2% to about 7%.

In embodiments of the invention, the composition comprises ecamsule at a concentration of about 0.5% to about 10% (w/w), homosalate at a concentration of about 0.5% to about 15% (w/w), sulisobenzone at a concentration of about 0.5% to about 10% (w/w) and octocrylene at a concentration of about 0.5% to about 1.0% (w/w).

In preferred embodiments of the invention, the composition comprises ecamsule at a concentration of about 1% to about 4% (w/w), homosalate at a concentration of about 2% to about 6% (w/w), sulisobenzone at a concentration of about 2% to about 4% (w/w) and octocrylene. at a concentration of about 2% to about %.

In embodiments of the invention, the composition comprises diethylamino hydroxybenzoyl hexyl benzoate at a concentration of about 0.5% to about 10% (w/w), homosalate at a concentration of about 0.5% to about 15% (w/w), octyl salicylate at a concentration of about 0.5% to about 10% (w/w) and octocrylene at a concentration of about 0.5% to about 10% (w/w).

In preferred embodiments of the invention, the composition comprises diethyl amino hydroxybenzoyl hexyl benzoate at a concentration of about 2% to about 5% (w/w), homosalate at a concentration of about 2% to about 4.9% (w/w), octyl salicylate at a concentration of about 1% to about 2.9% (w/w) and octocrylene at a concentration of about 2% to about 5%.

The compositions may also comprise stabilizers and antioxidants to help maintain the stability of the UVR filtering agents in the compositions, such as for example, benzotriazolyl dodecyl p-cresol (Tinogard TL or BDC) at a concentration of about 0.5% to about 4% (w/w) and diethylhexyl syringylidene malonate (DEHSM) at a concentration of about 0.5% to about 7% (w/w).

The sunscreen compositions of the present invention inhibit melanogenesis such that, despite the compositions allowing passage of a percentage of UVB in the wavelength range 290 nm-298 nm to be absorbed by the skin to produce vitamin D, melanin is not produced by the skin, and tanning (i.e., facultative pigmentation) does not occur. Advantageously, an individual may use the compositions of the present invention for extended periods of time without affecting their ability to produce vitamin D through the accumulation of a tan.

Melanin is responsible for skin coloration and is formed through a series of oxidative reactions involving the amino acid tyrosine and the enzyme tyrosinase. Tyrosinase converts tyrosine to L-3,4-dihydroxyphenylalanine (L-DOPA or DOPA) and then to dopaquinone. Subsequently, dopaquinone is converted to dopachrome through auto-oxidation, and then to dihydroxyindole (dihydroxyindole-2-carboxylic acid or DHICA) to form eumelanin (black-brown skin pigment). The latter reaction occurs in the presence of dopachrome tautomerase and DHICA oxidase. In the presence of cysteine or glutathione, dopaquinone is converted to cysteinyl DOPA or glutathione DOPA. Subsequently, pheomelanin (yellow-red skin pigment) is formed.

Melanogenesis inhibitors that may be used in the sunscreen compositions of the present invention disrupt at least one of these reactions, therein inhibiting melanin synthesis and pigmentation in the skin. Importantly, the preferred compounds that inhibit melanogenesis do not significantly block, absorb or reflect UVR in the wavelength range used by the skin to make vitamin D, and in particular, in the range of 290-298 nm.

In embodiments of the invention, the composition comprises a compound that inhibits melanogenesis by inhibiting tyrosinase activity when applied to the skin.

Non-limiting examples of appropriate compounds that inhibit tyrosinase activity that would be suitable for use in the compositions of the present invention include magnesium-L-ascorbyl-2-phosphate, licorice extract from glycyrrhiza glabra and glycyrrhiza uralensis comprising glabridin, N-undecylenoyl phenylalanine, 1-methylhydantoin-2-imide, phenylethyl resorcinol, trans-4-aminomethylcyclohexanecarboxylic acid, lactic acid, zinc glycinate, gluconic acid, dithiooctanediol, glucosamine, N-acetyl-D-glucosamine, oligopeptide-34, kojic acid, 4-hydroxyphenyl-alpha-D-glucopyranoside, palmaria palmata extract, glycolic acid, niacinamide and derivatives thereof, hydroxystilbene and derivatives thereof, aleosin, and hydroxyquinone and derivatives thereof.

In embodiments of the invention, the composition comprises a compound that inhibits melanogenesis by inhibiting the transfer of melanosomes when applied to the skin.

Non-limiting examples of appropriate compounds that suppress the transfer of melanosomes that would be suitable for use in the compositions of the present invention include niacinamide, palmaria palmate extract, flavonoid derivatives such as 5,7,3'-trihydroxy-3,6,4'-trimethoxyflavone and soy extracts that inhibit the PAR-2 pathway.

In embodiments of the invention, the composition comprises niacinamide at a concentration of about 0.5% to about 10% (w/w). In preferred embodiments of the invention, the composition comprises niacinamide at a concentration of about 1% to about 5%.

In embodiments of the invention, the composition comprises magnesium-L-ascorbyl-2-phosphate at a concentration of about 0.1% to about 12% (w/w). In preferred embodiments of the invention, the composition comprises magnesium-L-ascorbyl-2-phosphate at a concentration of about 1% to about 4.5% (w/w).

In embodiments of the invention, the composition comprises licorice extract from glycyrrhiza glabra and glycyrrhiza uralensis comprising glabridin at a concentration of about 0.1% to about 5% (w/w). In preferred embodiments of the invention, the composition comprises licorice extract from glycyrrhiza glabra and glycyrrhiza uralensis comprising glabridin at a concentration of about 1% to about 2.5% (w/w).

In embodiments of the invention, the composition comprises palmaria palmate extract at a concentration of about 0.5% to about 6% (w/w). In preferred embodiments of the invention, the composition comprises palmaria palmate extract at a concentration of about 1% to about 3% (w/w).

In embodiments of the invention, the composition comprises N-undecylenoyl phenylalanine at a concentration of about 0.1% to about 10% (w/w). In preferred embodiments of the invention, the composition comprises N-undecylenoyl phenylalanine at a concentration of about 0.25% to about 2.5% (w/w).

In embodiments of the invention, the composition comprises 1-methylhydantoin-2-imide at a concentration of about 0.05% to about 5% (w/w). In preferred embodiments of the invention, the composition comprises 1-methylhydantoin-2-imide at a concentration of about 0.25% to about 3% (w/w).

In embodiments of the invention, the composition comprises phenylethyl resorcinol at a concentration of about 0.05% to about 7% (w/w). In preferred embodiments of the invention, the composition comprises phenylethyl resorcinol at a concentration of about 0.1% to about 3% (w/w).

In embodiments of the invention, the composition comprises soy extracts at a concentration of about 0.5% to about 8% (w/w). In preferred embodiments of the invention, the composition comprises soy extracts at a concentration of about 1% to about 6% (w/w).

In embodiments of the invention, the composition comprises trans-4-aminomethylcyclohexanecarboxylic acid at a concentration of about 0.5% to about 3% (w/w). In preferred embodiments of the invention, the composition comprises trans-4-aminomethylcyclohexanecarboxylic acid at a concentration of about 1% to about 2% (w/w).

In embodiments of the invention, the composition comprises lactic acid or a derivative thereof at a concentration of about 1% to about 25% (w/w). In preferred embodiments of the invention, the composition comprises lactic acid or a derivative thereof at a concentration of about 4% to about 10% (w/w).

In embodiments of the invention, the composition comprises zinc glycinate at a concentration of about 0.05% to about 6% (w/w). In preferred embodiments of the invention, the composition comprises zinc glycinate at a concentration of about 0.1% to about 4% (w/w).

In embodiments of the invention, the composition comprises gluconic acid at a concentration of about 0.05% to about 5% (w/w). In preferred embodiments of the invention, the composition comprises gluconic acid at a concentration of about 0.5% to about 3% (w/w).

In embodiments of the invention, the composition comprises dithiooctanediol at a concentration of about 0.5% to about 6% (w/w). In preferred embodiments of the invention, the composition comprises dithiooctanediol at a concentration of about 1% to about 3% (w/w).

In embodiments of the invention, the composition comprises glucosamine at a concentration of about 0.5% to about 6% (w/w). In preferred embodiments of the invention, the composition comprises glucosamine at a concentration of about 1% to about 4% (w/w).

In embodiments of the invention, the composition comprises N-acetyl-D-glucosamine at a concentration of about 0.5% to about 6% (w/w). In preferred embodiments of the invention, the composition comprises N-acetyl-D-glucosamine at a concentration of about 0.75% to about 5% (w/w).

In embodiments of the invention, the composition comprises oligopeptide-34 at a concentration of about 0.1% to about 4% (w/w). In preferred embodiments of the invention, the composition comprises oligopeptide-34 at a concentration of about 1% to about 2% (w/w).

In embodiments of the invention, the composition comprises kojic acid and derivatives thereof at a concentration of about 0.5% to about 4% (w/w). In preferred embodiments of the invention, the composition comprises kojic acid and derivatives thereof at a concentration of about 1% to about 3% (w/w).

In embodiments of the invention, the composition comprises hydroxystilbenes and derivatives thereof at a concentration of about 0.1% to about 3% (w/w). In preferred embodiments of the invention, the composition comprises hydroxystilbenes and derivatives thereof at a concentration of about 0.25% to about 2% (w/w).

In embodiments of the invention, the composition comprises aleosin at a concentration of about 0.1% to about 3% (w/w). in preferred embodiments of the invention, the composition comprises aleosin at a concentration of about 0.25% to about 2% (w/w).

In embodiments of the invention, the composition comprises flavonoid derivatives such as 5,7,3'-trihydroxy-3,6,4'-trimethoxyflavone at a concentration of about 0.1% to about 3% (w/w). In preferred embodiments of the invention, the composition comprises flavonoid derivatives such as 5,7,3'-trihydroxy-3,6,4'-trimethoxyflavone at a concentration of about 0.25% to about 2% (w/w).

In embodiments of the invention, the composition comprises hydroquinone and derivatives thereof, such as monobenzyl ether of hydroquinone and harounoside, at a concentration of about 0.1% to about 3% (w/w). In preferred embodiments of the invention, the composition comprises hydroquinone and derivatives thereof, such as monobenzyl ether of hydroquinone and harounoside, at a concentration of about 0.25% to about 2% (w/w).

In preferred embodiments of the invention, the composition comprises at least one compound that inhibits melanogenesis selected from the group consisting of 1-methylhydantoine-2-imide, niacinamide, phenylethyl resorcinol, N-undecylenoyl phenylalanine, N-acetyl-D-glucosamine and magnesium-L-ascorbyl-2-phosphate.

In preferred embodiments of the invention, the composition comprises at least two compounds that inhibit melanogenesis selected from the group consisting of 1-methylhydantoine-2-imide, niacinamide, phenyl ethyl resorcinol, N-undecylenoyl phenylalanine, N-acetyl-D-glucosamine and magnesium-L-ascorbyl-2-phosphate.

For example, the composition may comprise 1-methylhydantoine-2-imide and niacinamide, or phenylethyl resorcinol and N-undecylenoyl phenylalanine, or N-acetyl-D-glucosamine and magnesium-L-ascorbyl-2-phosphate, or 1-methylhydantoine-2-imide and phenylethyl resorcinol, or N-undecylenoyl phenylalanine and N-acetyl-D-glucosamine, or magnesium-L-ascorbyl-2-phosphate and niacinamide, or niacinamide and N-acetyl-D-glucosamine, or magnesium-L-ascorbyl-2-phosphate and methylhydantoine-2-imide.

In embodiments of the invention, the composition comprises at least one compound that inhibits melanogenesis selected from the group consisting of 1-methylhydantoine-2-imide, niacinamide, phenylethyl resorcinol, N-undecylenoyl phenylalanine, N-acetyl-D-glucosamine, magnesium-L-ascorbyl-2-phosphate, wherein, when present, the composition comprises 1-methylhydantoin-2-imide at a concentration of about 0.05% to about 5% (w/w), the composition comprises niacinamide at a concentration of about 0.5% to about 10% (w/w), the composition comprises phenylethyl resorcinol at a concentration of about 0.05% to about 7% (w/w), the composition comprises N-undecylenoyl phenylalanine at a concentration of about 0.1% to about 10% (w/w), the composition comprises N-acetyl-D-glucosamine at a concentration of about 0.5% to about 6% (w/w), and the composition comprises magnesium-L-ascorbyl-2-phosphate at a concentration of about 0.1% to about 12% (w/w).

In embodiments of the invention, the composition comprises at least two compounds that inhibits melanogenesis selected from the group consisting of 1-methylhydantoine-2-imide, niacinamide, phenylethyl resorcinol, N-undecylenoyl phenylalanine, N-acetyl-D-glucosamine, magnesium-L-ascorbyl-2-phosphate, wherein, when present, the composition comprises 1-Methylhydantoin-2-imide at a concentration of about 0.05% to about 5% (w/w), the composition comprises niacinamide at a concentration of about 0.5% to about 10% (w/w), the composition comprises phenylethyl resorcinol at a concentration of about 0.05% to about 7% (w/w), the composition comprises N-undecylenoyl phenylalanine at a concentration of about 0.1% to about 10% (w/w), the composition comprises N-acetyl-D-glucosamine at a concentration of about 0.5% to about 6% (w/w), and the composition comprises magnesium-L-ascorbyl-2-phosphate at a concentration of about 0.1% to about 12% (w/w).

In embodiments of the invention, the composition comprises at least three compounds that inhibits melanogenesis selected from the group consisting of 1-methylhydantoine-2-imide, niacinamide, phenylethyl resorcinol, N-undecylenoyl phenylalanine, N-acetyl-D-glucosamine, magnesium-L-ascorbyl-2-phosphate, wherein, when present, the composition comprises 1-methylhydantoin-2-imide at a concentration of about 0.05% to about 5% (w/w), the composition comprises niacinamide at a concentration of about 0.5% to about 10% (w/w), the composition comprises phenylethyl resorcinol at a concentration of about 0.05% to about 7% (w/w), the composition comprises N-undecylenoyl phenylalanine at a concentration of about 0.1% to about 10% (w/w), the composition comprises N-acetyl-D-glucosamine at a concentration of about 0.5% to about 6% (w/w), and the composition comprises magnesium-L-ascorbyl-2-phosphate at a concentration of about 0.1% to about 12% (w/w).

In embodiments of the invention, the composition comprises 1-methylhydantoine-2-imide at a concentration of about 0.05% to about 5% (w/w) and niacinamide at a concentration of about 0.5% to about 10% (w/w).

In embodiments of the invention, the composition comprises phenylethyl resorcinol at a concentration of about 0.05% to about 7% (w/w) and N-undecylenoyl phenylalanine at a concentration of about 0.1% to about 10% (w/w).

In embodiments of the invention, the composition comprises N-acetyl-D-glucosamine at a concentration of about 0.5% to about 6% (w/w) and magnesium-L-ascorbyl-2-phosphate at a concentration of about 0.1% to about 12% (w/w).

In embodiments of the invention, the composition comprises 1-methylhydantoine-2-imide at a concentration of about 0.05% to about 5% (w/w) and phenylethyl resorcinol at a concentration of about 0.05% to about 7% (w/w).

In embodiments of the invention, the composition comprises N-undecylenoyl phenylalanine at a concentration of about 0.1% to about 10% (w/w) and N-acetyl-D-glucosamine at a concentration of about 0.5% to about 6% (w/w).

In embodiments of the invention, the composition comprises magnesium-L-ascorbyl-2-phosphate at a concentration of about 0.1% to about 12% (w/w) and niacinamide at a concentration of about 0.5% to about 10% (w/w).

In embodiments of the invention, the composition comprises niacinamide at a concentration of about 0.5% to about 10% (w/w) and N-acetyl-D-glucosamine at a concentration of about 0.5% to about 6% (w/w).

In embodiments of the invention, the composition comprises magnesium-L-ascorbyl-2-phosphate at a concentration of about 0.1% to about 12% (w/w) and 1-methylhydantoine-2-imide at a concentration of about 0.05% to about 5% (w/w).

In preferred embodiments of the invention, the composition comprises at least three compounds that inhibit melanogenesis selected from the group consisting of 1-methylhydantoine-2-imide, niacinamide, phenylethyl resorcinol, N-undecylenoyl phenylalanine, N-acetyl-D-glucosamine and magnesium-L-ascorbyl-2-phosphate.

For example, the composition may comprise 1-methylhydantoine-2-imide, niacinamide and phenylethyl resorcinol, or N-undecylenoyl phenylalanine, N-acetyl-D-glucosamine and magnesium-L-ascorbyl-2-phosphate, or 1-methylhydantoine-2-imide, phenylethyl resorcinol and N-undecylenoyl phenylalanine, or N-acetyl-D-glucosamine, magnesium-L-ascorbyl-2-phosphate and niacinamide, or niacinamide, phenylethyl resorcinol and N-acetyl-D-glucosamine, or magnesium-L-ascorbyl-2-phosphate, 1-methylhydantoine-2-imide and niacinamide, or phenyl ethyl resorcinol, N-acetyl-D-glucosamine and magnesium-L-ascorbyl-2-phosphate, or phenylethyl resorcinol, N-undecylenoyl phenylalanine, and magnesium-L-ascorbyl-2-phosphate.

In embodiments of the present invention, the composition comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In preferred embodiments of the present invention, the composition comprises 1-methylhydantoine-2-imide at a concentration of about 0.05% to about 2% (w/w), niacinamide at a concentration of about 0.5% to about 5% (w/w) and phenylethyl resorcinol at a concentration of about 0.05% to about 2% (w/w).

In embodiments of the invention, the composition comprises N-undecylenoyl phenylalanine at a concentration of about 0.1% to about 10% (w/w), N-acetyl-D-glucosamine at a concentration of about 0.5% to about 6% (w/w) and magnesium-L-ascorbyl-2-phosphate at a concentration of about 0.1% to about 12% (w/w).

In embodiments of the invention, the composition comprises 1-methylhydantoine-2-imide at a concentration of about 0.05% to about 5% (w/w), phenylethyl resorcinol at a concentration of about 0.05% to about 7% (w/w) N-undecylenoyl phenylalanine at a concentration of about 0.1% to about 10% (w/w).

In embodiments of the invention, the composition comprises N-acetyl-D-glucosamine at a concentration of about 0.5% to about 6% (w/w), magnesium-L-ascorbyl-2-phosphate at a concentration of about 0.1% to about 12% (w/w) and niacinamide at a concentration of about 0.5% to about 10% (w/w).

In embodiments of the invention, the composition comprises niacinamide at a concentration of about 0.5% to about 10% (w/w), phenylethyl resorcinol at a concentration of about 0.05% to about 7% (w/w) and N-acetyl-D-glucosamine at a concentration of about 0.5% to about 6% (w/w).

In embodiments of the invention, the composition comprises magnesium-L-ascorbyl-2-phosphate at a concentration of about 0.1% to about 12% (w/w), 1-methylhydantoine-2-imide at a concentration of about 0.05% to about 5% (w/w) and, niacinamide at a concentration of about 0.5% to about 10% (w/w).

In embodiments of the invention, the composition comprises phenylethyl resorcinol at a concentration of about 0.05% to about 7% (w/w), N-acetyl-D-glucosamine at a concentration of about 0.5% to about 6% (w/w) and magnesium-L-ascorbyl-2-phosphate at a concentration of about 0.1% to about 12% (w/w).

In embodiments of the invention, the composition comprises phenylethyl resorcinol at a concentration of about 0.05% to about 7% (w/w), N-undecylenoyl phenylalanine at a concentration of about 0.1% to about 10% (w/w), and magnesium-L-ascorbyl-2-phosphate at a concentration of about 0.1% to about 12% (w/w).

In preferred embodiments of the invention, the compositions include one of more UVR filtering agents and one or more compounds that inhibit melanogenesis, and the agent(s), compound(s) and their respective concentrations are chosen and adapted such that composition prevents UVR-induced skin damage, allows passage of sufficient UVB in the range of 290 nm-298 nm to produce Vitamin D, and inhibits the formation of melanin, when applied to the skin.

In embodiments of the invention, the compositions comprise one or more UVR filtering agents that are chemical sun screening agents that absorb UVR selected from the group consisting of menthyl anthranilate, sulisobenzone (benzophenone-4), sulisobenzone sodium (benzophenone-5), diethylamino hydroxybenzoyl hexyl benzoate, oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), Polysilicone-15 (dimethico-diethylbenzal malonate), disodium phenyl dibenzimidazole tetrasulfonate, PEG-25 PABA (Ethoxylated ethyl 4-aminobenzoate), homosalate (homomenthyl salicylate) and octyl salicylate, (ethylhexyl salicylate); and one or more compounds that inhibit melanogenesis selected from the group consisting of magnesium-L-ascorbyl-2-phosphate, licorice extract from glycyrrhiza glabra and glycyrrhiza uralensis comprising glabridin, N-undecylenoyl phenylalanine, 1-methylhydantoin-2-imide, phenylethyl resorcinol, trans-4-aminomethyl-cyclohexanecarboxylic acid, lactic acid, zinc glycinate, gluconic acid, dithiooctanediol, glucosamine, N-acetyl-D-glucosamine, oligopeptide-34, kojic acid and derivatives thereof, hydroxystilbene and derivatives thereof, aleosin, hydroxyquinone and derivatives thereof, niacinamide, palmaria palmate extract, flavonoid derivatives such as 5,7,3'-trihydroxy-3,6,4'-trimethoxyflavone and soy extracts that inhibit the PAR-2 pathway.

In embodiments of the present invention, the composition comprises at least one UVA filtering agent selected from the group consisting of menthyl anthranilate, diethylamino hydroxybenzoyl hexyl benzoate, ecamsule (terephthalylidene dicamphor sulfonic acid), butyl methoxy dibenzoylmethane (avobenzone), and disodium phenyl dibenzimidazole tetrasulfonate; at least one UVB filtering agent selected from the group consisting of sulisobenzone (benzophenone-4), sulisobenzone sodium (benzophenone-5), oxybenzone (benzophenone-3), octocrylene (2-ethylhexyl alpha-cyano-beta-phenylcinnamate), Polysilicone-15 (dimethicodiethylbenzal malonate). PEG-25 PABA (Ethoxylated ethyl 4-aminobenzoate), homosalate (homomenthyl salicylate) and octyl salicylate (ethylhexyl salicylate); and at least one compound that inhibits melanogenesis selected from the group consisting of 1-methylhydantoine-2-imide, niacinamide, phenylethyl resorcinol, N-undecylenoyl phenylalanine, N-acetyl-D-glucosamine and magnesium-L-ascorbyl-2-phosphate.

In embodiments of the present invention, the composition comprises at least one UVA filtering agent selected from the group consisting of menthyl anthranilate, diethylamino hydroxybenzoyl hexyl benzoate, ecamsule (terephthalylidene dicamphor sulfonic acid), butyl methoxy dibenzoylmethane (avobenzone), and disodium phenyl dibenzimidazole tetrasulfonate; at least two UVB filtering agents selected from the group consisting of sulisobenzone (benzophenone-4), sulisobenzone sodium (benzophenone-5), oxybenzone (benzophenone-3), octocrylene (2-ethylhexyl alpha-cyano-beta-phenylcinnamate), Polysilicone-15 (dimethicodiethylbenzal malonate), PEG-25 PABA (Ethoxylated ethyl 4-aminobenzoate), homosalate (homomenthyl salicylate) and octyl salicylate (ethylhexyl salicylate) and at least two compounds that inhibits melanogenesis selected from the group consisting of 1-methylhydantoine-2-imide, niacinamide, phenylethyl resorcinol, N-undecylenoyl phenylalanine, N-acetyl-D-glucosamine and magnesium-L-ascorbyl-2-phosphate.

In preferred embodiments of the present invention, the composition comprises at least two UVR filtering agents selected from the group consisting of oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), homosalate (homomenthyl salicylate) and octyl salicylate (ethyl hexyl salicylate), wherein, when present, the composition comprises oxybenzone (benzophenone-3) at a concentration of about 1% to about 4% (w/w), the composition comprises ecamsule (terephthalylidene dicamphor sulfonic acid) at a concentration of about 1% to about 9% (w/w), the composition comprises octocrylene (2-ethylhexyl alpha-cyano-beta-phenylcinnamate) at a concentration of about 1% to about 7% (w/w), the composition comprises butyl methoxy dibenzoylmethane (avobenzone) at a concentration of about to about 5% (w/w), the composition comprises homosalate (homomenthyl salicylate) at a concentration of about 0.5% to about 6% (w/w), the composition comprises octyl salicylate (ethylhexyl salicylate) at a concentration of about 0.5% to about 6% (w/w), and the composition comprises at least one compound that inhibits melanogenesis selected from the group consisting of 1-methylhydantoine-2-imide, niacinamide, phenylethyl resorcinol, N-undecylenoyl phenylalanine, N-acetyl-D-glucosamine, magnesium-L-ascorbyl-2-phosphate, wherein, when present, the composition comprises 1-methylhydantoin-2-imide at a concentration of about 0.05% to about 5% (w/w), the composition comprises niacinamide at a concentration of about 0.5% to about 10% (w/w), the composition comprises phenylethyl resorcinol at a concentration of about 0.05% to about 7% (w/w), the composition comprises N-undecylenoyl phenylalanine at a concentration of about 0.1% to about 10% (w/w), the composition comprises N-acetyl-D-glucosamine at a concentration of about 0.5% to about 6% (w/w), and the composition comprises magnesium-L-ascorbyl-2-phosphate at a concentration of about 0.1% to about 12% (w/w).

In preferred embodiments of the present invention, the composition comprises at least three UVR filtering agents selected from the group consisting of oxybenzone (benzophenone-3), ecamsule (terephthalylidene dicamphor sulfonic acid), octocrylene (2-ethylhexyl alpha-cyano-beta-phenylcinnamate), butyl methoxy dibenzoylmethane (avobenzone), homosalate (homomenthyl salicylate) and octyl salicylate (ethylhexyl salicylate), wherein, when present, the composition comprises oxybenzone (benzophenone-3) at a concentration of about 1% to about 4% (w/w), the composition comprises ecamsule (terephthalylidene dicamphor sulfonic acid) at a concentration of about 1% to about 9% (w/w), the composition comprises octocrylene (2-ethylhexyl alpha-cyano-beta-phenylcinnamate) at a concentration of about 1% to about 7% (w/w), the composition comprises butyl methoxy dibenzoylmethane (avobenzone) at a concentration of about 1% to about 5% (w/w), the composition comprises homosalate (homomenthyl salicylate) at a concentration of about 0.5% to about 6% (w/w), the composition comprises octyl salicylate (ethylhexyl salicylate) at a concentration of about 0.5% to about 6% (w/w), and the composition comprises at least two compounds that inhibits melanogenesis selected from the group consisting of 1-methylhydantoine-2-imide, niacinamide, phenylethyl resorcinol, N-undecylenoyl phenylalanine, N-acetyl-D-glucosamine, magnesium-L-ascorbyl-2-phosphate, wherein, when present, the composition comprises 1-methylhydantoin-2-imide at a concentration of about 0.05% to about 5% (w/w), the composition comprises niacinamide at a concentration of about 0.5% to about 10% (w/w), the composition comprises phenyl ethyl resorcinol at a concentration of about 0.05% to about 7% (w/w), the composition comprises N-undecylenoyl phenylalanine at a concentration of about 0.1% to about 10% (w/w), the composition comprises N-acetyl-D-glucosamine at a concentration of about 0.5% to about 6% (w/w), and the composition comprises magnesium-L-ascorbyl-2-phosphate at a concentration of about 0.1% to about 12% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises at least one compound that inhibits melanogenesis selected from the group consisting of 1-methylhydantoine-2-imide, niacinamide, phenylethyl resorcinol, N-undecylenoyl phenylalanine, N-acetyl-D-glucosamine and magnesium-L-ascorbyl-2-phosphate.

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises 1-methylhydantoine-2-imide at a concentration of about 0.05% to about 5% (w/w) and niacinamide at a concentration of about 0.5% to about 10% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises phenylethyl resorcinol at a concentration of about 0.05% to about 7% (w/w) and N-undecylenoyl phenylalanine at a concentration of about 0.1% to about 10% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises N-acetyl-D-glucosamine at a concentration of about 0.5% to about 6% (w/w) and magnesium-L-ascorbyl-2-phosphate at a concentration of about 0.1% to about 12% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises 1-methylhydantoine-2-imide at a concentration of about 0.05% to about 5% (w/w) and phenylethyl resorcinol at a concentration of about 0.05% to about 7% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises N-undecylenoyl phenylalanine at a concentration of about 0.1% to about 10% (w/w) and N-acetyl-D-glucosamine at a concentration of about 0.5% to about 6% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises magnesium-L-ascorbyl-2-phosphate at a concentration of about 0.1% to ab 12% (w/w) and niacinamide at a concentration of about 0.5% to about 10% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises niacinamide at a concentration of about 0.5% to about 10% (w/w) and IN-acetyl-D-glucosamine at a concentration of about 0.5% to about 6% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises magnesium-L-ascorbyl-2-phosphate at a concentration of about 0.1% to about 12% (w/w) and 1-methylhydantoine-2-imide at a concentration of about 0.05% to about 5% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises 1-methylhydantoine-2-imide at a concentration of about 0.05% to about 2% (w/w), niacinamide at a concentration of about 0.5% to about 5% (w/w) and phenylethyl resorcinol at a concentration of about 0.05% to about 2% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises N-undecylenoyl phenylalanine at a concentration of about 0.1% to about 10% (w/w), N-acetyl-D-glucosamine at a concentration of about 0.5% to about 6% (w/w) and magnesium-L-ascorbyl-2-phosphate at a concentration of about 0.1% to about 12% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises 1-methylhydantoine-2-imide at a concentration of about 0.05% to about 5% (w/w), phenylethyl resorcinol at a concentration of about 0.05% to about 7% (w/w) N-undecylenoyl phenylalanine at a concentration of about 0.1% to about 10% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises N-acetyl-D-glucosamine at a concentration of about 0.5% to about 6% (w/w), magnesium-L-ascorbyl-2-phosphate at a concentration of about 0.1% to about 12% (w/w) and niacinamide at a concentration of about 0.5% to about 10% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises niacinamide at a concentration of about 0.5% to about 10% (w/w), phenylethyl resorcinol at a concentration of about 0.05% to about 7% (w/w) and N-acetyl-D-glucosamine at a concentration of about 0.5% to about 6% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises magnesium-L-ascorbyl-2-phosphate at a concentration of about 0.1% to about 12% (w/w), 1-methylhydantoine-2-imide at a concentration of about 0.05% to about 5% (w/w) and, niacinamide at a concentration of about 0.5% to about 10% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises phenylethyl resorcinol at a concentration of about 0.05% to about 7% (w/w), N-undecylenoyl phenylalanine at a concentration of about 0.1% to about 10% (w/w), and magnesium-L-ascorbyl-2-phosphate at a concentration of about 0.1% to about 12% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% to about 10% (w/w), octocrylene at a concentration of about 0.5% to about 10% (w/w), and further comprises phenylethyl resorcinol at a concentration of about 0.05% to about 7% (w/w), N-acetyl-D-glucosamine at a concentration of about 0.5% to about 6% (w/w), and magnesium-L-ascorbyl-2-phosphate at a concentration of about 0.1% to about 12% (w/w).

In embodiments of the present invention, the composition comprises at least one UVA filtering agent selected from the group consisting of menthyl anthranilate, diethylamino hydroxybenzoyl hexyl benzoate, ecamsule (terephthalylidene dicamphor sulfonic acid), butyl methoxy dibenzoylmethane (avobenzone), and disodium phenyl dibenzimidazole tetrasulfonate; at least one UVB filtering agent selected from the group consisting of sulisobenzone (benzophenone-4)), sulisobenzone sodium (benzophenone-5), oxybenzone (benzophenone-3), octocrylene (2-ethylhexyl alpha-cyano-beta-phenylcinnamate), (dimethicodiethylbenzal malonate), PEG-25 PABA (Ethoxylated ethyl 4-aminobenzoate), homosalate (homomenthyl salicylate) and octyl salicylate (ethylhexyl salicylate), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In embodiments of the invention, the composition comprises avobenzone at a concentration of about 0.5% to about 7% (w/w), oxybenzone at a concentration of about 0.5% to about 8% (w/w), octyl salicylate at a concentration of about 0.5% to about 10% (w/w) and octocrylene at a concentration of about 0.5% to about 10% (w/w), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In embodiments of the invention, the composition comprises avobenzone at a concentration of about 0.5% to about 7% (w/w), homosalate at a concentration of about 0.5% to about 15% (w/w), octyl salicylate at a concentration of about 0.5% in about 10% (w/w) and, sulisobenzone at a concentration of about 0.5% to about 10% (w/w), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In embodiments of the invention, the composition comprises menthyl anthranilate at a concentration of about 0.5% to about 7% (w/w), homosalate at a concentration of about 0.5% to about 15% (w/w), oxybenzone at a concentration of about 0.5% to about 8% (w/w) and octocrylene at a concentration of about 0.5% to about 10% (w/w), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In embodiments of the invention, the composition comprises ecamsule at a concentration of about 0.5% to about 10% (w/w), homosalate at a concentration of about 0.5% to about 15% (w/w), sulisobenzone at a concentration of about 0.5% to about 10% (w/w) and octocrylene at a concentration of about 0.5% to about 10% (w/w), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

In embodiments of the invention, the composition comprises diethylamino hydroxybenzoyl hexyl benzoate at a concentration of about 0.5% to about 10% (w/w), homosalate at a concentration of about 0.5% to about 15% (w/w), octyl salicylate at a concentration of about 0.5% to about 10% (w/w) and octocrylene at a concentration of about 0.5% to about 10% (w/w), and further comprises 1-methylhydantoine-2-imide at a concentration of about 0.05% to about 5% (w/w), niacinamide at a concentration of about 0.5% to about 10% (w/w) and phenylethyl resorcinol at a concentration of about 0.05% to about 7% (w/w).

It would be understood that any compounds or components at concentrations that would effectively filter UVB in the range of 290 nm-298 nm would be inappropriate for inclusion in the compositions of the present invention.

Similarly, any compounds or components that effectively encouraged the formation of melanin in the skin would be inappropriate for inclusion in the compositions of the present invention.

The following are non-limiting examples of melanogenesis inhibitors which, at certain concentrations, may be inappropriate for the sunscreen compositions of the present invention in that they effectively filter UVB in the range used by the skin to make vitamin D.

Melanogenesis inhibitors that are inappropriate for inclusion in the compositions of the present invention include retinoids and derivatives thereof, ronaflair Softshade, corticosteroids include topical steroids, such as fluocinolone, 5,7-dihydroxy-6,8-dimethyl-3-(4-methoxybenzylchroman-4-one, hydroxycinnamic acids are phenylpropanoids, panax ginseng and panax quinquefolius extracts, 2,5-dihydrobenzoic acid, 3,4,5-trihydroxybenzoate, 4-(benzyloxy)phenol, N-acetyl-4-S-cysteaminylphenol and N-propionyl-4-S-cysteaminylphenol, 4-hydroxyanisole, salicylic acid and acetylsalicylic acid, aloin, camellia sinensis extract, yitis Vinifera extract. Inappropriate UV filtering agents The following UVR filtering agents, at certain concentrations, are inappropriate for inclusion in the compositions of the present invention because they substantially filter LAIR in the vitamin D producing range. These inappropriate UV filters include, but are not limited to: benzophenone (diphenylmethanone), benzophenone-1 (2,4-dihydroxybenzophenone), benzophenone-2 (2,2',4,4'-tetrahydroxybenzophenone), benzophenone-6 (2,2'-dihydroxy-4,4'-dimethoxybenzophenone), benzophenone-8 (2,2'-dihydroxy-4-methoxybenzophenone), benzophenone-12 (2-hydroxy-4-octyloxybenzophenone), benzophenone-7 (5-chloro-2-hydroxybenzophenone), benzophenone-11 (bis (2,4-ihydroxypheny)methanone), 4-methylbenzylidene camphor (Uvinul MBC 95 or 3-(4-methylbenzyliden)camphor), cinoxate (2-ethoxyethyl p-methoxycinnamate), octinoxate (octyl methoxycinnamate or ethylhexyl methoxycinnamate), diethanolamine p-methoxycinnamate, isoamyl p-methoxycinnamate (Neo Heliopan E1000), ferulic acid, dibenzoylmethane (dibenzoyl methane), bisoctrizole (Tinosorb M, methylene bis-benzotriazolyl tetramethyl butyl phenol or MBBT), zinc oxide (ZnO), titanium dioxide (titanium (IV) oxide or TiO2), cerium (IV) oxide (CeO2), ensulizole (2-phenylbenzimidazole-5-sulfonic acid or Parsol HS), phenylbenzimidazole tea sulfonate, sodium phenylbenzimidazole sulfonate, 2-phenylbenzimidazole, aminobenzoic acid (4-aminobenzoic acid, p-aminobenzoic acid or PABA), padimate-O (ethylhexyl dimethyl PABA or 2-ethylhexyl 4-dimethylaminobenzoate), padimate-A (amyl p-dimethylaminobenzoate or amyl dimethyl PABA), glyceryl aminobenzoate (glyceryl 1-4-aminobenzoate or glyceryl PABA), ethylhexyl triazone (octyl triazone or ethylhexyl triazone), trolamine salicylate (triethanolamine salicylate or TEA salicylate), drometrizole trisiloxane (Mexoryl XL or 2-(2-Hydroxy-5-methyl-phenyl)benzotriazole), benzotrizinol (Tinosorb S or bis-ethylhexyloxyphenol methoxyphenyl triazine), iscotrizinol (diethylhexyl butamido triazone or Uvasorb HEB), digalloyl trioleate (5-(3,3-dimethyl 2 norbornyliden)-3penten-2-one or gallic acid), camphor benzalkonium methosulfate, (Mexoryl SO1), benzylidene camphor sulfonic acid, polyacrylamido methylbenzylidene camphor, 6,7-dihydroxycoumarin (Aesculetin), 7-hydroxycoumarin (Umbelliferone), brown algae polyphenols (BAPs), ethyl 4-[bis(hydroxyl propyl)] aminobenzoate (propoxylate of p-aminoethylbenzoate or roxadimate), ethyl cinnamate, ethyl dihydroxypropyl PABA, ethyl diisopropylcinnamate, ethyl methoxycinnamate, ethyl PABA (Benzocaine), ethyl urocanate, glyceryl ethylhexanoate dimethoxycinnamate, glyceryl octanoate dimethoxycinnamate, isopropylbenzyl salicylate, isopentyl trimethoxycinnamate trisiloxane, isopropyl methoxycinnamate, diisopropyl methyl cinnamate, lawsone, magnesium aluminum menthyl salicylate, 2,4-dihydroxy-N-(3-hydroxypropyl)-3,3-dimethylbutanamide ester, benzyl salicylate, petrolatum jelly, Quicksun Clear and Quicksun Matte extracts, and urocanic acid (4-imidazoleacrylic acid); diacylglycerol analogues, forskolin, isobutylmethylxanthine, and melanocyte-stimulating hormone.

It would be understood by the person skilled in the art that the composition of the invention can also include preservatives, humectants, emollient, moisturizers, consistency factors, chelating agents, fragrance, active agents, excipients, diluents and coloring agents.

Moisturizers and humectants used in the compositions of the present invention may make the skin softer, more pliable and thicker, thereby enhancing the skin's ability to produce vitamin D. In preferred embodiments, the compositions of the present invention comprise glycerin and/or panthenol and/or derivatives thereof. The glycerin may be at a concentration of about 0.1% to about 8% (w/w). The panthenol may be at a concentration of about 0.05% to about 7% (w/w).

Other appropriate moisturizers and humectants for the sunscreen compositions of the present invention include, are not limited to, water, amino acids, ceramides, ceramide 2, hyaluronic acid, fatty acids, triglycerides, phospholipids, glycosphingolipids, linoleic acid, glycosaminoglycans, glycerin (AKA glycerin), mucopolysaccharide, pyrrolidone carboxylic acid, alpha hydroxy acids, lanolin, lipids, apricot oil, canola oil, corn oil, jojoba oil, jojoba wax, lecithin, olive oil, safflower oil, sesame oil, soybean oil, rapeseed oil, flaxseed oil, sweet almond oil, walnut oil, palm oil, linseed oil, Cannabis sativa seed oil, squalane, propylene glycol dicaprylate/dicaprate, cetyl alcohol, sodium cetearyl sulfate, cetearyl alcohol, decylene cetyl hydroxyethylcellulose, triglyceride, acrylates/steareth-20 methacrylate copolymer, panthenol, calcium pantothenate, pantothenic acid, sorbitan stearate, probiotics with active bacteria cultures, and silicone-derived ingredients such as cyclomethicone, dimethicone crosspolymer, silicone, and dimethicone.

The compositions of the present invention may also include one or more of the following appropriate excipients, dilutents, emollients, thickeners, preservatives, plasticisers and vehicles: Hydrolite-5, SymGlucan, beta-glucans, oat beta-glucan, pentylene glycol, Vaccinium myrtillus (bilberry) extract, jojoba oil, cranberry seed oil, fireweed extract, black current oil, Rubus occidentalis (black raspberry), Tilia cordata (linden) flower extract, peony root extract, glycine soja oil, Borago officials seed oil, allantoin, Ilex paraguariensis (yerba mate) extract, Olea europaea (olive) fruit oil, hydrogenated olive oil, Camellia japonica, honeysuckle flower extract, palmitoyl tripeptide-5, palmitoyl tetrapeptide-7, Persicaria hydropiper, ceramide 2, carnosine, Terminalia catappa, dill extract, hydrolyzed glycosaminoglycans, Gentiana lutea root extract, Arctium lappa, Leontopodium alpinum extract, kudzu root, flaxseed oil, bisabol, Epilobium angustifolium extract, genistein, Poria cocos extract (fu ling), bladderwrack (seaweed) extract, Persea gratissima (avocado) oil, Centella asiatica (gotu kola) hydrocotyl extract, glycosphingolipid or natural moisturizing factor (NMF), squalene, Elaeis guineensis (palm) oil, lactoperoxidedase, ellagic acid, geranium extract, Medicago sativa (alfalfa) extract, Brassica campestris (rapeseed) oil, aquaporins, lecithin, almond oil, 1-carnitine, Argania spinosa (argan) oil, lotus seed extract, Centaurea cyanus (cornflower) extract, egg yolk, canola oil, ceramides, blackberry extracts, Curcuma longa (turmeric) root, linseed oil, Passifflora edulis seed oil, inositol, oleanolic acid, lycopene, granatum extract, Rubus ursinus and R. idaeus (boysenberry) berry extract, Calluna vulgaris flower (heather) extract, xanthophyll, marshmallow extract, glycosaminoglycans, Arachis hypogaea (peanut) extract, chamomile, matricaria (chamomile) oil, lutein, Cucurbitea peponis (pumpkin), gromwell, chitosan, Tamarindus indica seed extract, phospholipids (cephalin), caprylic/capric triglyceride, beta-sitosterol, heolen (mushroom), Rosa roxburghii (chestnut) rose extract, honey, glutamine, Spiraea ulmaria (meadowsweet) extract, corn oil, creatine, Eriobotrya japonica (loquat) extract, glutathione, burdock root extract, Euterpe oleraca (acai) extracts, apricot kernel oil, Cucumis melo (honeydew melon) fruit extract, Coffea arabica (coffee) seed extract, caffeic acid, palm oil, Mangifera indica (mango) seed butter, kukui nut oil, Oenothera biennis (evening primrose) oil, yucca extract, tannic acid, carrageenan (seaweed) gum, arachidyl alcohol, locust bean gum, zeolite, polysorbates, polysorbate 80, polysorbate, 20, bis-PEG-18 methyl ether dimethyl silane, hydrolyzed wheat protein, sodium cetearyl sulfate, cetearyl alcohol, decylene glycol, PPG-20 methyl glucose ether, oleth 10, VP/hexadecane copolymer, Solarium tuberosum (potato starch) extract, Larrea tridentate (chaparral) extract, gelatin, ethylenediaminetetraacetic acid (EDT), disodium EDTA, oleic acid, hydrolysed silk, red 6 lake, phytic acid, dicaprylyl carbonate, sodium PEG olive oil carboxylate, melibiose, cyclomethicone, Astrocaryum murumuru seed butter, neopentyl glycol dicaprylate/dicaprate, ethyl macadamiate, caramel, rice bran oil, ethyl methylpropanediol, dogwood extract, noni juice, diethylhexyl carbonate, red 33, carmine, Corylus americana (hazelnut) oil, disodium glyceryl phosphate, PEG 12 buteth-16, PEG-26 buteth-26, dimethicone crosspolymer, dimethicone, silicone, cetyl hydroxyethylcellulose, triglyceride, acrylates/steareth-20 methacrylate copolymer, calcium pantothenate (pantothenic acid), sorbitan stearate, triodyldodecyl citrate, chlorella (algae), di-PPG-3 myristyl ether adipate, PPG-2 myristyl ether propionate, casein (milk protein), Ahnfeltia concinna (algae) extract, lauryl alcohol, hydrogenated didecane, sodium dehydroacetate, milk vetch (huang qi) root, Cannabis sativa seed oil, Bertholletia excelsa (Brazil nut) extract, cyclotetrasiloxane, methyl gluceth-20, C13-14 isoparaffin, tridecyl trimellitate, castor oil, glyceryl myristate, parabens including methylparaben, propylparaben, butylparaben, and ethylparaben, magnesium, PEG-19 rapeseed sterol, escin, potassium phosphate, batyl alcohol, polyisobutene, bentonite, bismuth oxychloride, boron nitride, calcium carbonate, carnauba wax, China clay (kaolin), Copernicia cerifera wax, cornstarch, fuller's earth, montmorillonite, nylon-12, potassium, rice starch, silica, silicate, silk powder, silt, sodium carbonate, bis-diglyceryl polyacyladipate, dulse, ceteareth-20, acetyl hexapeptide-3, walnut oil, sorbitan sesquioleate, tetrasodium etidronate, pecan oil, propylene glycol laurate, propylene glycol stearate, propylene dimethicone, purified water, demineralized water, soluble fish collagen, sodium carbomer, isostearic acid, PEG-14 butyl ether, poloxamer 184, cocoglycerides, natto gum, decyl oleate, sodium laureth-13 cathoxylate, laureth-4, colostrum, guar gum, hydroxypropyl guar, sclerotium gum, chlorophene, xymenynic acid, behenic acid, aminomethyl propanol, dextrin, nonoxynols, trilaurin, polyglyceryl methacrylate, polyacrylamide, glycerol monostearate, sebacic acid, PEG-32, sodium hexametaphosphate, erythrulose, sorbitan oleate, diisopropyl dimer dilinoleate, cetyl alcohol, steareth-20, phytantriol, glycereth-26, glycereth-26 phosphate, ethylhexylglycerin, dihydroxyacetone (DHA), glyceryl stearate, cetearyl ethylhexanoate (cetearyl alcohol), glycerol trioleate, pectin, ammonium laureth sulfate, cholecalciferol, acrylates/C10-30 alkyl acrylate crosspolymer, yellow 5, 1,2-Hexanediol, PEG/PPG-17/6 copolymer, phosphoric acid, wheat germ oil, wheat protein, propylene glycol isostearate, ricinoleate, acetyl tyrosine, polyglycerol monostearate, lauryl PEG-9 polydimethylsiloxyethyl dimethicone, whey protein, dimethyl capramide, behentrimonium chloride, hydrogenated polyisobutene, dipentaerythrityl hexacaprylate/hexacaprate, acrylates copolymer, xylose, sodium acrylate/acryloydimethyl taurate copolymer, C18-36 acid triglyceride, monton wax, laureth-7, sorbitol, stearyl methicone, sodium myreth sulfate, butyl acetate, PEG-80 sorbitan laurate, boron nitrate, stearyl alcohol, diisopropyl adipate, dimethicone copolyol, tridecyl stearate, glyceryl oleate, glyceryl isostearate, cetyl acetate, xanthan gum, caprylyl glycol, chloroxylenol, carbopol, elastin, isododecane, polybutene, isostearamide DEA, cetyl esters, tetrasodium EDTA, polyethylene, PEG/PPG-20/15 dimethicone, candelilla, sorbic acid, laureth-23, ethylhexyl stearate, potassium sorbate, PEG 90M, PEG-12 dimethicone, ergocalciferol, carnosol acid, triethanolamine, pycnogenol, glyceryl distearate, C20-40 pareth-40, polysorbate 60, dimethicone/PEG-10/15 crosspolymer, polyglyceryl-6 isostearate, sesame oil, PEG-10 dimethicone, PEG/PPG-18/4 copolymer, cetyl PEG/PPG-101-dimethicone, PEG-8, octyl stearate, disodium diglyceryl phosphate, paraffin, trisodium EDTA, PEG-10 dimethicone/vinyl dimethicone crosspolymer, dextran, NaPCA, folic acid, glycol stearate, xylitol isohexadecane, panthenol, cocamide DEA and MEA, and bismuth oxychloride.

In embodiments of the invention, in addition to the UVR filtering agents and melanogenesis inhibitors, the compositions of the present invention may comprise one of more compounds selected from the group consisting of glycerin at a concentration of about 0.1% to 7%, panthenol at a concentration of about 0.05% to 7%; an acrylate/C10-30 alkyl acrylate crosspolymer at a concentration of about 0.25% to 5%, a caprylic/capric triglyceride at a concentration of about 0.25% to 5%, carbomer at a concentration of about 0.25% to 5%, dimethicone at a concentration of about 0.25% to 5%, dimethyl capramide at a concentration of about 0.25% to 5%, disodium EDTA at a concentration of about 0.25% to 5%, ethylhexyl methoxycrylene at a concentration of about 0.25% to 5%, ethylhexyl palmitate at a concentration of about 0.25% to 5%, ethylhexylglycerin at a concentration of about 0.25% to 5%, phenoxyethanol at a concentration of about 0.25% to 5%, sorbitan sesquioleate at a concentration of about 0.25% to 5%, stearic acid at a concentration of about 0.25% to 5%, stearyl alcohol at a concentration of about 0.25% to 5% and triethanolamine at a concentration of about 0.25% to 5%.

Definitions

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

In the context of this specification the term "about" will be understood as indicating the usual tolerances that a skilled addressee would associate with the given value.

In the context of this specification, where a range is stated for a parameter, it will be understood that the parameter includes all values within the stated range, inclusive of the stated endpoints of the range.

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

DETAILED DESCRIPTION

Although the invention has been described with reference to certain embodiments detailed herein, other embodiments can achieve the same or similar results. Variations and modifications of the invention will be obvious to those skilled in the art and the invention is intended to cover all such modifications and equivalents.

The present invention is further described by the following non-limiting examples.

Preparing Compositions

Examples of the compositions of the present invention have been prepared according to the following method.

1.) Dry blend in advance flaked or powdered ingredients before dispersing into the oil phase by mixing together 1-methylhydantoin-2-imide, ethylhexyl methoxycrylene, ethylhexyl palmitate, acrylates/C10-30 alkyl acrylate crosspolymer, triethanolamine, sorbitan sesquioleate, avobenzone, homosalate, octyl salicylate, and octocrylene.

2.) In a separate container, disperse into the water phase by mixing together dimethyl capramide, caprylic/capric triglycerides, dimethicone, disodium EDTA, carbomer, phenylethyl resorcinol, niacinamide, glycerin, panthenol, phenoxyethanol, and ethylhexylglycerin.

3.) Mix oil and water phases together, and add stearyl alcohol, and stearic acid to the mixture, before slowly heating to between 47 and 82° C. with continual mixing until the product is homogeneous.

4.) Allow the end product to cool to room temperature and seal in containers.

Preliminary Study

A preliminary study was performed to test the abilities of three possible combinations of UV filters used the sunscreen compositions of the present invention to effectively filter harmful UVR and prevent sun damage. The study was performed using the protocols prescribed by the US Food and Drug Administration (FDA 21 CFR Parts 201 and 310) to determine SPF values, and conducted by Bioscreen Testing Services, Inc. of Torrance, Calif., USA.

The compositions included in the study were:

Sample A (SPF 15): 3% (w/w) avobenzone, 4.9% (w/w) homosalate, 2.3% (w/w) octyl salicylate, and 2.7% (w/w) octocrylene.

Sample B (SPF 30): 3% (w/w) avobenzone, 4.9% (w/w) homosalate, 3.7% (w/w) octyl salicylate, and 2.7% (w/w) octocrylene.

Sample C (SPF 50): 3% (w/w) avobenzone, 6% (w/w) homosalate, 4% (w/w) octyl salicylate, and 7% (w/w) octocrylene.

Sample D (control; SPF 30): 8% (w/w) octyl methoxycinnamate, 3.5% (w/w) 4-methylbenzylidene camphor, 2% (w/w) avobenzone and 2% (w/w) octocrylene Sample E (control; SPF 30): 25% (w/w) zinc oxide 25%, 6% (w/w) octyl methoxycinnamate, 1% (w/w) 4-methylbenzylidene camphor.

Sample F (control; SPF 50): 9% (w/w) octocrylene, 5.7% (w/w) titanium dioxide, 5% (w/w) oxybenzone, 4.5% (w/w) avobenzone, 4.5% (w/w) octyl salicylate, 4.5% (w/w) homosalate and 1.5% (w/w) bemotrizinol.

Sample G (control; SPF 50): 8% (w/w) octocrylene, 3% (w/w) octyl triazone, 4% (w/w) butyl methoxydibenzoylmethane and 8% (w/w) homosalate.

Compositions A, B or C were evenly applied to the backs 10 adult human subjects in the amount of 2 mg/cm$^2$ and allowed to dry for 15 to 30 minutes. Subjects were then exposed to 1 minimum erythema dose (MED) of UV light from a Xenon arc simulator. Subjects returned to the facility 16 to 24 hours after exposure at which time a technician visually graded the exposure sites for erythema. Each of the compositions prevented erythema.

The compositions A to G were also smeared on clear silica plates, and UVB light from a lamp was shone through them, and the percentages of light that passed through the plates were detected and recorded at the other end. The percentages of UVB light at a wavelength of 295 nm that were transmitted through each of the above plates were: Sample A 23.1%, Sample B 15.8%, Sample C 13.8%, Sample D 0.8%, Sample F 0.2%. Sample F 0.3%, and Sample G 1.0%.

The preliminary study also examined the abilities compositions A, B and C to permit vitamin D production when compared to conventional sunscreens (compositions D, B, F and G). This vitamin D production study was an original in vitro experiment conducted in the laboratories of Dermatest, Pty Ltd of Sydney, Australia.

Vitamin D intake is often measured in International Units (IU). One minimum erythema dose (MED) of mid-day sunlight shone directly on most of the body of a middle-aged person with healthy type I or type II skin (i.e., Caucasian) will result in the production of between 10,000 and 20,000 IU of vitamin D. Based on the results of this study, it can be calculated that the same middle-aged Caucasian person receiving the same MED would produce vitamin D in the following amounts while wearing the tested compositions: Sample A between 2310 and 4620 IU, Sample B between 1580 and 3160 IU, Sample C between 1380 and 2760 IU, Sample D between 80 and 160 IU, Sample E between 20 and 40 IU, and Sample G between 90 and 180 IU.

Study 1

A study was conducted at the Vitamin D Skin and Bone Research Laboratory, Department of Medicine, Boston University Medical Center by Michael F. Holick, PhD, MD., titled "Comparative performance of a skin whitening product for vitamin D production". The study used sunscreen compositions of the present invention with an SPF 30, and the objective was to determine if the compositions permitted efficient synthesis of provitamin D under experimental conditions.

Materials and methods: A fluorescent lamp with high ultraviolet output was used to irradiate borosilicate ampoules containing the vitamin D precursor 7-dehydrocholesterol (7-DHC) beneath a layer of polyethylene (Saran) wrap with 2 mg/cm 2 of the following compositions:

Formula 1000: 3% (w/w) avobenzone, 4.9% (w/w) homosalate, 2.3% (w/w) salicylate, 2.7% (w/w) octocrylene, 1.5%

(w/w) 1-methylhydantoin-2-imide, 1% (w/w) phenylethyl resorcinol, 3% (w/w) niacinamide, 3.5% (w/w) glycerin, 0.5% (w/w) panthenol, water, dimethyl capramide, ethyl hexyl methoxycrylene, ethylhexyl palmitate, caprylic/capric triglycerides, stearyl alcohol, stearic acid, dimethicone, disodium EDTA, acrylates/C10-30 alkyl acrylate crosspolymer, phenoxyethanol, carbomer, triethanol amine, sorbitan sesquioleate, and ethylhexylglycerin.

Formula 2000: 3% (w/w) avobenzone, 4.9% (w/w) homosalate, 2.3% (w/w) octyl salicylate, 2.7% (w/w) octocrylene, 1.5% (w/w) 1-methylhydantoin-2-imide, 1% (w/w) phenylethyl resorcinol, 3% (w/w) niacinamide, 1.75% (w/w) glycerin, 0.25% (w/w) panthenol, water, dimethyl capramide, ethylhexyl methoxycrylene, ethylhexyl palmitate, caprylic/capric triglycerides, stearyl alcohol, stearic acid, dimethicone, disodium EDTA, acrylates/C10-30 alkyl acrylate crosspolymer, phenoxyethanol, carbomer, triethanolamine, sorbitan sesquioleate, and ethylhexylglycerin; or Formula 3000: 3% (w/w) avobenzone, 4.9% (w/w) homosalate, 2.3% (w/w) octyl salicylate, 2.7% (w/w) octocrylene, 1.5% (w/w) 1-methylhydantoin-2-imide, 1% (w/w) phenylethyl resorcinol, 3% (w/w) niacinamide, 7% (w/w) glycerin, 1% (w/w) panthenol, water, dimethyl capramide, ethylhexyl methoxycrylene, ethylhexyl palmitate, caprylic/capric triglycerides, stearyl alcohol, stearic acid, dimethicone, disodium EDTA, acrylates/C10-30 alkyl acrylate crosspolymer, phenoxyethanol, carbomer, triethanolamine, sorbitan sesquioleate, and ethylhexylglycerin.

A 45-minute time course of exposure at 15-minute intervals was conducted. Ampoule contents were analyzed by high performance liquid chromatography (HPLC). Two samples of each were taken and averaged. The results showed representative chromatograms of ampoule contents exposed to UVB radiation through polyethylene film with either formula topically applied, wherein previtamin D3 production can be calculated from the area under the curves of the relevant chromatograms. There was a larger area under the curve for conversion to previtamin D3 after 15, 30, and 45 minutes exposure to UVB using Formula 2000 (1.24, 2.58, and 3.39), and Formula 1000 (1.24, 2.34, and 3.17), and Formula 3000 (1.21. 2.3. and 2.59).

Study 2

A further study entitled "Skin-whitening, dark-spot reducing and wrinkle-improving effects of five topical formulas: a blinded and placebo-controlled clinical trial in healthy adult men and women" was performed using sunscreen compositions of the present invention, namely formulas 1000, 2000 and 3000 described above, as well as the following controls.

Formulas 4000 (melanogenesis inhibitors only): 1.5% (w/w) 1-methylhydantoin-2-imide, 1% (w/w) phenylethyl resorcinol, 3% (w/w) niacinamide, water, dimethyl capramide, ethyl hexyl methoxycrylene, ethylhexyl palmitate, caprylic/capric triglycerides, stearyl alcohol, stearic acid, dimethicone, disodium EDTA, acrylates/C10-30 alkyl acrylate crosspolymer, phenoxyethanol, carbomer, triethanolamine, sorbitan sesquioleate, and ethylhexylglycerin.

Formula 5000 (no active ingredients): 3.5% (w/w) glycerin, 0.5% (w/w) panthenol, water, dimethyl capramide, ethylhexyl methoxycrylene, ethylhexyl palmitate, caprylic/capric triglycerides, stearyl alcohol, stearic acid, dimethicone, disodium EDTA, acrylates/C10-30 alkyl acrylate crosspolymer, phenoxyethanol, carbomer, triethanolamine, sorbitan sesquioleate, and ethylhexylglycerin.

Subjects and methods: Healthy men and women ages 18 to 79 years, skin types I through V were enrolled. Subjects topically applied 0.8 g of one of five randomly assigned compositions to the back of one hand (active hand) and nothing to the other hand (control hand) in the morning and the evening daily for 12 weeks. The following changes in skin appearance were recorded: "Skin Whitening" which included skin lightening, and skin tone; "Dark Spot(s)" which included age spots, sunspots, and liver spots and "Wrinkles" which included fine lines, the number of wrinkles, and the size of wrinkles. Subjects self-assessed changes in the appearance of their skin on a paper or electronic diary from the previous week for 12 consecutive weeks using a subjective score from minus 3 (i.e., darker skin, darker spot, or more wrinkles) to positive 3 (i.e., lighter skin, lighter spot, or fewer wrinkles).

Results: The subject-reported scores for "Skin Whitening" and "Dark Spot(s)" were each summed and averaged for each of the 12 weeks. Formula 1000 had n=3, Formula 2000 had n=2, Formula 3000 had n=2, Formula 4000 had n=4, and Formula 5000 had n=3. The results below may be viewed using a within-group analysis of variance that compares differences over time between active and control hands for each of the five formulas. Alternately, the results below may be viewed using a between-group analysis of variance that compares differences over time between Formula 5000 group or Formula 4000 group and each of the other three active formula groups.

Skin Whitening weekly means for Formula 1000 group:
ACTIVE hand Week 1 (Wk1) 0, Wk2 0, Wk3 0.66, Wk4 0.66, Wk5 0.66, Wk6 0.66, Wk7 1, Wk8 0.66, Wk9 1.33, Wk10 1.66, Wk11 1.5, and Wk12 1.5.
CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Skin Whitening weekly means for Formula 2000 group:
ACTIVE hand Wk1 0, Wk2 0, Wk3 0, Wk4 0, Wk5 0, Wk6 0, Wk7 0, Wk8 0, Wk9 0.5, Wk10 0.5, Wk11 1, and Wk12 1.
CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Skin Whitening weekly means for Formula 3000 group:
ACTIVE hand Wk1 0, Wk2 0, Wk3 0, Wk4 0.5, Wk5 1, Wk6 0.5, Wk7 0.5, Wk8 0.5, Wk9 0.5, Wk10 2, Wk11 2, and Wk12 2.
CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Skin Whitening weekly means for Formula 4000 group:
ACTIVE hand Wk1 0, Wk2 0, Wk3 0, Wk4 0, Wk5 0, Wk6 0, Wk7 0.25, Wk8 0, Wk9 0.33, Wk10 0, Wk11 −0.33, and Wk12 −0.33.
CONTROL hand: Wk1 0, Wk2 0, Wk3 0, Wk4 0, Wk5 0, Wk6 0, Wk7 −0.025, Wk8 0, Wk9 0, Wk10 0, Wk11 −0.33, and Wk12 −0.33.

Skin Whitening weekly means for Formula 5000 group:
ACTIVE hand Wk1 0, W2 0, Wk3 0, Wk4 0, Wk5 0, Wk6 0, Wk7 0, Wk8 0, Wk9 0, Wk10 0, Wk11 0, and Wk12 0.
CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Dark Spot(s) weekly means for Formula 1000 group:
ACTIVE hand Week 1 (Wk1) 0, Wk2 0, Wk3 0.5, Wk4 1, Wk5 1, Wk6 0.66, Wk7 1, Wk8 1, Wk9 1.33, Wk10 1.66, Wk11 1.5, and Wk12 1.5.

CONTROL hand: Week 1 (Wk1) 0, Wk2 0, Wk3 0, Wk4 0, Wk5 0, Wk6 0, Wk7 0, Wk8 0, Wk9 0, Wk10 0, Wk11 0, and Wk12 0.

Dark Spot(s) weekly means for Formula 2000 group:

ACTIVE hand Wk1 0, Wk2 0, Wk3 0.5, Wk4 0, Wk5 0.5, Wk6 0, Wk7 0, Wk8 0.5, Wk9 0.5, Wk10 1, Wk11 1, and Wk12 1.

CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Dark Spot(s) weekly means for Formula 3000 group:

ACTIVE hand Wk1 0, Wk2 0, Wk3 0, Wk4 0.5, Wk5 0.5, Wk6 0.5, Wk7 0.5, Wk8 0.5, Wk9 0.5, Wk10 2, Wk11 2, and Wk12 2.

CONTROL hand: Wk1 0, Wk2 0, Wk3 0, Wk4 0, Wk5. 0, Wk6 0, Wk7 0, Wk8 0, Wk9 0, Wk10 0, Wk11 0, and Wk12 0.

Dark Spot(s) weekly means for Formula 4000 group:

ACTIVE hand Wk1 0, Wk2 0, Wk3 0, Wk4 0, Wk5 0, Wk6 0, Wk7 0.25, Wk8 0, Wk9 0.33, Wk10 −0.33, Wk11 −0.33, and Wk12 −0.33.

CONTROL hand: Wk1 0, Wk2 0, Wk3 0, Wk4 0, Wk,5 0, Wk6 0, Wk7 0, Wk8 −0.25, Wk9 0, Wk10 0, Wk11 −0.33, and Wk12 −0.33.

Dark Spot(s) weekly means for Formula 5000 group:

ACTIVE hand Wk1 0, Wk2 0, Wk3 0, Wk4 0, Wk5 0, Wk6 0, Wk7 0, Wk8 0, Wk9 0, Wk10 0, Wk11 0, and Wk12 0.

CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Wrinkles weekly means for Formula 1000 group:

ACTIVE hand Week 1 (Wk1) 0, Wk2 0.33, Wk3 0.66, Wk4 0.66, Wk5 0.66, Wk6 0.66, Wk7 0.33, Wk8 0.66, Wk9 0.66, Wk10 0.66, Wk11 0.33, and Wk12 0.33.

CONTROL hand: Week 1 (Wk1) 0, Wk2 0, Wk3 0, Wk4 0, Wk5 0, Wk6 0, Wk7 0, Wk8 0, Wk9 0, Wk10 0, Wk11 0, and Wk12 0.

Wrinkles weekly means for Formula 2000 group:

ACTIVE hand Wk1 0, Wk2 0, Wk3 0, Wk4 0, Wk5 0, Wk6 0, Wk7 0, Wk8 0, Wk9 0, Wk10 0, Wk11 0, and Wk12 0.

CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Wrinkles weekly means for Formula 3000 group:

ACTIVE hand Wk1 0.5, Wk2 0.5, Wk3 0.5, Wk4 1, Wk5 1, Wk6 1, Wk7 0.5, Wk8 0.5, Wk9 0.5, Wk10 2, Wk11 2, and Wk12 2.

CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

Wrinkles weekly means for Formula 4000 group:

ACTIVE hand Wk1 0, Wk2 0, Wk3 0, Wk4 0, Wk5 0, Wk6 0, Wk7 0.25, Wk8 0, Wk9 0.33, Wk10 −0.33, Wk11 −0.33, and Wk12 −0.33.

CONTROL hand: Wk1 0, Wk2 0, Wk3 0, Wk4 0, W5 0, Wk6 0, Wk7 0.25, Wk8 0, Wk9 0.33, Wk10 0.33, Wk11 0, and Wk12 0.

Wrinkles weekly means for Formula 5000 group:

ACTIVE hand Wk1 0, Wk2 0, Wk3 0, Wk4 0.33, Wk5 0, Wk6 0.33, Wk7 0.33, Wk8 0.33, Wk9 0.33, Wk10 0.33, Wk11 0.33, and Wk12 0.33.

CONTROL hand: Wk1 0, Wk2 0, Wk3 0, Wk4 0, Wk5 0, Wk6 0, Wk7 0, Wk8 0, Wk9 0, Wk10 0, Wk11 0, and Wk12 0.

In summary, subject diaries for show that for the active hands (Formulas 1000, 2000, and 3000) starting at about week 3 or week 4 there were on average improvements in skin lightening, and dark spots; and that these improvements became more pronounced up to week but there were essentially no changes for the control groups. There were no reports of adverse events.

Study 3

A study titled "A comparison of the percentages of transmissions of vitamin D producing wavelengths through skincare lotions" was commissioned and conducted by Dermatest TecConsult, Pty Ltd in Sydney, Australia. The study measured how much UVR, at different wavelengths passed through ten topical formulations.

The compositions include in the study were Formula 1000 (SPF 15), Formula 2000 (SPF 15), and Formula 4000 (as described in Study 1 above); and five commercially available skin brightening products with SPF as follows:

i. Garnier Skinactive BB Cream Renews with SPF 15 (octinoxate 4%, titanium dioxide 2.1%, ascorbyl glucoside);

ii. Peter Thomas Roth CC Cream Complexion Corrector SPF 30 (titanium dioxide 10.26%, zinc oxide 5.76%, hydroquinone-alpha-D-glucopyranoside and myrciaria dubia);

iii. Diorsnow Brightening Illuminating SPF 30 (zinc oxide 18.7%, octinoxate 7.49%, titanium dioxide 2.13%, oxybenzone 2%, ascorbyl glucoside);

iv. Neutrogena Essential Soy Helps Reduce Blotchiness and the Look of Dark Spots SPF 30 (avobenzone 3%, homosalate 12%, octyl salicylate 5%, octocrylene 1.7%, oxybenzone 3%, glycine soja seed extract, mica); and v. La Roche-Posay CC Cream Daily Complete Tone Correcting Cream SPF 30 (octinoxate 3%, octyl salicylate 3.5%, octocrylene 4.5%, titanium dioxide 6.2%, mica). A further control, a sunscreen that permits vitamin D production without brightening agents, was included:

vi. Solar D Sunscreen SPF 15 (Formula DP100-181B avobenzone 3%, homosalate 4.9%, octyl salicylate 2.3%, octocrylene 2.7%).

The study compositions were applied at 1.3 mg/cm$^2$ in precisely controlled amounts with a uniform distribution over the roughened side of transparent plates (Moulded PMMA 6 um Helioscreen plates). Four samples of each concentration of each product were prepared and studied. UV light was shone through each plate with product applied and the percentage of UV light that was transmitted through the sample was measured at the other end by an instrument (Shimadzu UV-2450 Spectrophotometer fitted with Integrating Sphere Device). A total of 16 measurements were taken for each study product. The mean transmission values for each wavelength from 290 nm to 400 nm were determined.

Results: Formulas 1000 and 2000 allow the passage of approximately 23% and 21.5%, respectively, of the UVR in the wavelength range of 290 nm-298 nm. Formula 4000 (without SPF) does not provide safe protection from the sun and transmits 64.9 percent in the 290 nm to 298 nm range.

None of the five commercial comparators permit a biologically significant amount of wavelengths in the vitamin D forming range to be transmitted. Formula (i) only allows the passage of approximately 1.8% of the UVR in the wavelength range of 290 nm-298 nm. Formula (ii) only allows the passage of approximately 1% of the UVR in the wavelength range of 290 nm-298 nm. Formula (iii) only allows the passage of approximately 1% of the UVR in the wavelength range of 290 nm-298 nm. Formula (iv) only allows the passage of approximately 5.3% of the UVR in the wavelength range of 290 nm-298 nm. Formula (v) only allows the passage of approximately 3.5% of the UVR in the wavelength range of 290 nn-298 nm.

Formula (vi) allows the passage of approximately 23.5% of the UVR in the wavelength range of 290 nm-298 nm. That there was little difference between the results obtained for Formulas 1000, 2000 and (vi) shows that the melanogenesis inhibitors and other inactive ingredients in Formulas 1000 and 2000 do not significantly inhibit the passage of the wavelengths in the vitamin D forming range.

The invention claimed is:

1. A topical sunscreen composition to prevent facultative pigmentation and protect skin from sun damage while permitting the skin to produce vitamin D, the composition comprising:
   a combination of UVR filtering agents, wherein the combination and concentrations of the UVR filtering agents is adapted to selectively filter enough light in UVA and UVB rangers to prevent UVR-induced skin damage while permitting passage of at least 10% of UVB in a range of approximately 290 nm-298 nm to permit vitamin D production, wherein the combination of UVR filtering agents include
      octocrylene at a concentration of about 0.5% to about 10% (w/w), and
      butyl methoxy dibenzoylmethane at a concentration of about 0.5% to about 7% (w/w),
      homosalate at a concentration of about 0.5% to about 15% (w/w), and
      octyl salicylate at a concentration of about 0.5% to about 10% (w/w); and
   a combination of melanogenesis inhibition compounds, wherein the combination and concentrations of the melanogenesis inhibition compounds is adapted to inhibit melanogenesis and the corresponding facultative pigmentation of the skin even though the skin absorbs the at least 10% of UVB in the range of approximately 290 nm-298 nm, wherein the absorption of the UVB in the range of approximately 290 nm-298 nm by the skin typically results in production of melanin by the skin and the corresponding facultative pigmentation of the skin in addition to vitamin D production, wherein the facultative pigmentation of the skin reduces the vitamin D production when the skin absorbs the UVB in the range of approximately 290 nm-298 nm so inhibiting the facultative pigmentation of the skin increases the vitamin D production when the skin absorbs the at least 10% of UVB in the range of approximately 290 nm-298 nm, wherein the composition does not include any ingredients at concentrations that would effectively filter UVB in the range of approximately 290 nm-298 nm, and wherein the combination of melanogenesis inhibition compounds include 1-methylhydantoin-2-imide, niacinamide, and phenylethyl resorcinol.

2. The topical sunscreen composition of claim 1, wherein the combination of UVR filtering agents include the octocrylene at a concentration of between 0.5% and 7% (w/w).

3. The topical sunscreen composition of claim 1, wherein the combination of UVR filtering agents include the butyl methoxy dibenzoylmethane at a concentration of between 1% and 5% (w/w).

4. The topical sunscreen composition of claim 1, wherein the combination of UVR filtering agents include the homosalate at a concentration of between 0.5% and 6% (w/w).

5. The topical sunscreen composition of claim 1, wherein the combination of UVR filtering agents include the octyl salicylate at a concentration of between 0.5% and 6% (w/w).

6. The topical sunscreen composition of claim 1, wherein the combination of melanogenesis inhibition compounds inhibit melanogenesis by inhibiting tyrosinase activity when applied to the skin.

7. The topical sunscreen composition of claim 1, wherein the combination of melanogenesis inhibition compounds includes 1-methylhydantoin-2-imide at a concentration of between 0.05% and 5% (w/w).

8. The topical sunscreen composition of claim 1, wherein the combination of melanogenesis inhibition compounds includes niacinamide at a concentration of about 0.5% to about 10% (w/w).

9. The topical sunscreen composition of claim 1, wherein the combination of melanogenesis inhibition compounds includes phenylethyl resorcinol at a concentration of between 0.05% and 7% (w/w).

10. The topical sunscreen composition of claim 1, further comprising glycerin at a concentration of between 0.25% and 8% (w/w).

11. The topical sunscreen composition of claim 1, further comprising panthenol at a concentration of between 0.25% and 10% (w/w).

12. A topical sunscreen composition to prevent facultative pigmentation and protect skin from sun damage while permitting the skin to produce vitamin D, the composition comprising:
   a combination of UVR filtering agents including octocrylene, butyl methoxy dibenzoylmethane, homosalate, and octyl salicylate, wherein concentrations of the UVR filtering agents is adapted to prevent UVR-induced skin damage while permitting passage of at least 10% of UVB in a range of approximately 290 nm-298 nm to permit vitamin D production; and
   a combination of melanogenesis inhibition compounds including 1-methylhydantoin-2-imide at a concentration of about 0.05% to about 5% (w/w), niacinamide at a concentration of about 0.5% to about 10% (w/w), and phenylethyl resorcinol at a concentration of about 0.05% to about 7% (w/w), wherein the combination and concentrations of the melanogenesis inhibition compounds is adapted to inhibit melanogenesis and the corresponding facultative pigmentation of the skin that typically occurs when the skin absorbs the UVB in the range of approximately 290 nm-298 nm, wherein the facultative pigmentation of the skin reduces vitamin D production when the skin absorbs the UVB in the range of approximately 290 nm-298 nm so inhibiting the facultative pigmentation of the skin increases vitamin D production when the skin absorbs the at least 10% of UVB in the range of approximately 290 nm-298 nm.

13. The topical sunscreen of claim 12, wherein the combination of UVR filtering agents include
   the octocrylene at a concentration of about 0.5% to about 10% (w/w),
   the butyl methoxy dibenzoylmethane at a concentration of about 0.5% to about 7% (w/w),
   the homosalate at a concentration of about 0.5% to about 15% (w/w), and
   the octyl salicylate at a concentration of about 0.5% to about 10% (w/w).

14. The topical sunscreen of claim 12, wherein the combination of UVR filtering agents include
   the octocrylene at a concentration of approximately 2.7% (w/w),
   the butyl methoxy dibenzoylmethane at a concentration of approximately 3% (w/w), the homosalate at a concentration of approximately 4.9% (w/w), and the octyl salicylate at a concentration of approximately 2.3% (w/w).

15. The topical sunscreen of claim 12, wherein the combination of melanogenesis inhibition compounds include the 1-methylhydantoin-2-imide at a concentration of approximately 1.5% (w/w), the niacinamide at a concentration of approximately 3.0% (w/w), and the phenylethyl resorcinol at a concentration of approximately 1.0% (w/w).

* * * * *